Figure 1:
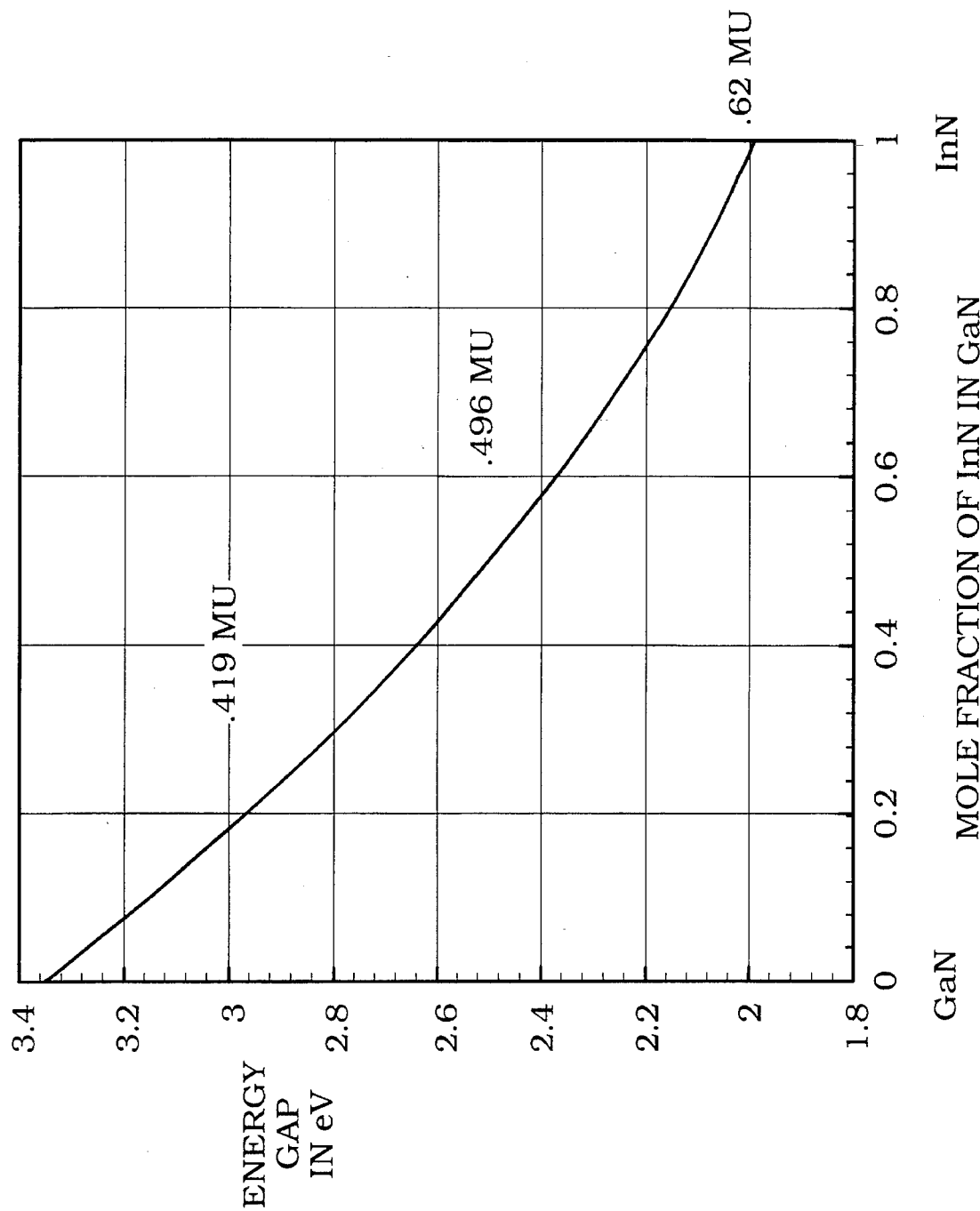

United States Patent [19]
Kuehnle et al.

[11] Patent Number: 5,534,056
[45] Date of Patent: *Jul. 9, 1996

[54] COMPOSITE MEDIA WITH SELECTABLE RADIATION-TRANSMISSION PROPERTIES

[75] Inventors: Manfred R. Kuehnle, Waldesruh, P.O. Box 1020, Rte. 103A, New London, N.H. 03257; Hermann Statz, Wayland, Mass.

[73] Assignee: Manfred R. Kuehnle, New London, N.H.

[*] Notice: The term of this patent shall not extend beyond the expiration date of Pat. No. 5,5,527,386.

[21] Appl. No.: 144,249

[22] Filed: Oct. 28, 1993

[51] Int. Cl.$^6$ ............................................. C08K 3/00
[52] U.S. Cl. ........................... 106/455; 106/403; 106/419; 106/425; 106/437; 106/452; 106/481; 106/22 C; 106/499; 424/59; 424/401; 252/584; 252/586; 252/588
[58] Field of Search ................................. 252/584, 586, 252/588; 106/499, 419, 425, 437, 452, 455, 403, 481, 400, 401, 22 C; 424/401, 59

[56] References Cited

U.S. PATENT DOCUMENTS

| | | | |
|---|---|---|---|
| 2,977,477 | 3/1961 | Rosi et al. | 252/584 |
| 4,652,755 | 3/1987 | Solomon et al. | 250/341 |
| 4,820,016 | 4/1989 | Cohen et al. | 350/96.29 |
| 4,944,936 | 7/1990 | Lawhorne | 423/612 |
| 5,008,143 | 4/1991 | Armanini | 428/207 |
| 5,037,476 | 8/1991 | Degani et al. | 106/436 |
| 5,106,437 | 4/1992 | Lau et al. | 156/51 |
| 5,152,229 | 10/1992 | Nimmo | 106/400 |
| 5,190,583 | 3/1993 | Menzel et al. | 106/241 |
| 5,215,580 | 6/1993 | Elfenthal et al. | 106/441 |
| 5,232,970 | 8/1993 | Sole et al. | 524/404 |
| 5,238,607 | 8/1993 | Herron et al. | 252/518 |
| 5,256,191 | 10/1993 | Thompson et al. | 106/19 A |
| 5,280,169 | 1/1994 | Honey et al. | 250/216 |
| 5,317,454 | 5/1994 | Sharp et al. | 359/886 |
| 5,318,628 | 6/1994 | Matijevic et al. | 106/499 |

FOREIGN PATENT DOCUMENTS

| | | |
|---|---|---|
| 0230303 | 7/1987 | European Pat. Off. |
| 2033418 | 5/1980 | United Kingdom. |
| 2104528 | 3/1983 | United Kingdom. |

OTHER PUBLICATIONS

Abstract of Japanese Patent No. JP2173622. Jul. 1990.
Abstract of Japanese Patent No. JP59223754. Dec. 1984.
Abstract of Japanese Patent No. JP54083955. Jul. 1979.
van de Hulst, H. C., "Light Scattering by Small Particles", Dover Publications, NY (1957), pp. 9, 269–281; QC 431 H8. (no month available).

*Primary Examiner*—Anthony Green
*Assistant Examiner*—Scott L. Hertzog
*Attorney, Agent, or Firm*—Cesari and McKenna

[57] ABSTRACT

Radiation-absorptive materials, suitable for fabrication into packages, sheets, inks, paints, decorative surface treatments, lotions, creams, and gels are disclosed. The materials exploit certain optical properties associated with uniform, spherical, nanosize particles to provide complete radiation absorption, over a selected bandwidth, at low concentration. One type of particle exhibits an "absorption edge" at a chosen wavelength, transmitting radiation whose wavelength exceeds the characteristic bandgap wavelength, while effectively absorbing all radiation with wavelengths smaller than that minimum. Another type of particle exhibits "optical resonance," which causes radiation of a characteristic wavelength to interact with the particles so as to produce self-reinforcing internal reflections that strongly enhance the amplitude of the radiation trapped within the particle.

41 Claims, 23 Drawing Sheets

COMPOSITE MEDIA WITH SELECTABLE RADIATION-TRANSMISSION PROPERTIES

BACKGROUND OF THE INVENTION

A. Field of the Invention

The present invention relates to the selective absorption of electromagnetic radiation in small particles, and more particularly to solid and liquid composite materials that absorb strongly within a chosen, predetermined portion of the electromagnetic spectrum while remaining substantially transparent outside this region.

B. Description of the Related Art

Transparent and translucent materials such as glass, plastic, gels, and viscous lotions have for many years been combined with coloring agents to alter their optical transmission properties. Agents such as dyes and pigments absorb radiation within a characteristic spectral region and confer this property on materials in which they are dissolved or dispersed. Selection of the proper absorptive agent facilitates production of a composite material that blocks transmission of undesirable light frequencies.

Beer bottles, for example, contain additives that impart a green or brown color to protect their contents from decomposition. These include iron (II) and iron (III) oxides in the case of glass bottles, while any of a variety of dyes can be employed in plastic containers. The concentration of these additives (in weight percent relative to the surrounding carrier material) is generally very heavy, in the range of 1–5%, resulting in high expense, difficult dispersion within the carrier, and the need to employ special mixing techniques to counter strong agglomeration tendencies.

Most commercially useful coloring agents absorb across a range of frequencies; their spectra typically feature steady decrease from a peak wavelength of maximum absorption, or $\lambda_{max}$. When mixed into a host carrier, such materials tend to produce fairly dark composite media with limited overall transmission properties, since the absorption cannot be "tuned" precisely to the undesirable frequencies. If used as a container, for example, such media provides relatively poor visibility of the contents to an observer.

Traditional means of forming particles that may serve as coloring agents include chemical precipitation and mechanical production (e.g., so-called atomizing) processes. These processes frequently fail to reliably maintain uniform particle size due to agglomeration, and cause sedimentation during and/or after the particles are generated. The problem of agglomeration becomes particularly acute at very small particle diameters, where the ratio of surface area to volume becomes very large and adhesion forces favor agglomeration as a mechanism of energy reduction.

While suitable for conventional uses, in which radiation absorption is imprecise and largely unrelated to particle size or morphology, non-uniform particles cannot be employed in more sophisticated applications where size has a direct impact on performance.

DESCRIPTION OF THE INVENTION

A. OBJECTS OF THE INVENTION

Accordingly, it is an object of the present invention to provide an alloyed, multielement material capable of selective absorption within a sharply defined segment of the electromagnetic spectrum.

It is a further object of the invention to introduce a selectable, sharply defined radiation-absorption edge into a carrier material using advantageously small amounts of particulate material dispersed throughout the carrier material.

It is another object of the invention to introduce into a carrier material particles having hypergeometric absorption cross-sections within a selectable, defined band of the electromagnetic spectrum.

It is still another object of the invention to confer selectable radiation-absorption properties to carrier materials without objectionable scattering of visible light.

It is yet another object of the invention to obtain very thorough, equidistant dispersion of particulate additives within a carrier material by supplying each particle with an electrostatic charge to cause mutual repulsion during the manufacturing or application process.

Still another object of the invention is to provide a manufacturing process that facilitates production of stoichiometrically and compositionally defined particulate materials in large quantities and at precise, uniform sizes and shapes.

Yet another object of the invention is to create uniformly sized (i.e., monodispersed) particles in the vapor phase and treat them during manufacture so as to permanently charge them electrostatically and freeze them temporarily in a cryogenically cooled receptor.

Still another object of the invention is to create novel radiation-absorptive containers, packages, sheets, inks, paints, decorative surface treatments, lotions, creams, and gels.

Other objects will, in part, be obvious and will, in part, appear hereinafter. The invention accordingly comprises an article of manufacture possessing the features and properties exemplified in the constructions described herein and the several steps and the relation of one or more of such steps with respect to the others and the apparatus embodying the features of construction, combination of elements and the arrangement of parts that are adapted to effect such steps, all as exemplified in the following summary and detailed description, and the scope of the invention will be indicated in the claims.

B. BRIEF SUMMARY OF THE INVENTION

The present invention exploits certain radiation-absorption properties of select semiconductor materials to produce highly advantageous optical properties in uniform, spherical, nanosize particles. These particles are used as optical transmission/reflection "control agents" for a variety of products that require sharp transitions between regions of high and low absorption, i.e., where the material is largely transparent and where it is largely opaque. One aspect of the invention includes the ability to confer an optical "absorption edge" at a chosen wavelength on a product using very small amounts of nanosize particulate material dispersed in a carrier substance. While the small size of the particles assures virtually complete transmission of radiation whose wavelength exceeds the characteristic bandgap wavelength, the particles effectively absorb all radiation with wavelength smaller than that minimum.

In a second aspect, the present invention exploits a physical feature of certain nanosize spherical particles. "Optical resonance" causes radiation of a characteristic wavelength to interact with the particles so as to produce self-reinforcing internal reflections that strongly enhance the amplitude of the radiation trapped within the particle. Although absorption (as opposed to trapping) of the radiation is unnecessary to create the resonance effect, particles that do exhibit some intrinsic absorption will show a dramatic increase at resonance wavelengths. Optically resonant particles tend to have relatively large refraction indices, and these preferably differ significantly from the carrier in which the material is dispersed.

To utilize either of these phenomena, a uniform distribution of particles within the carrier is highly desirable in order to maximize the absorptive effect (that is, to assure isotropic absorption and to minimize the amount of material that must be used). The present invention preferably accomplishes this by addition of the particles at an early stage of production, and/or by providing individual particles with an electrostatic charge to create mutual repulsion during manufacture and dispersion within a carrier. The invention includes a preferred technique and an apparatus for particle manufacture, based on vapor-phase generation of precisely sized liquid droplets, which are charged electrostatically as they solidify and are frozen in a cryogenically cooled receptor.

The present invention enables production of entire classes of novel radiation-absorptive containers, packages, sheets, inks, paints, decorative surface treatments, lotions, creams, and gels.

C. BRIEF DESCRIPTION OF THE DRAWINGS

The foregoing discussion will be understood more readily from the following detailed description of the invention, when taken in conjunction with the accompanying drawings, in which:

FIG. 1 graphically illustrates, by way of example utilizing GaN and InN, the relationship between constituent mole fraction in a GaN/InN alloy and bandgap energies as the fraction is varied, shifting the bandgap across the visible spectrum;

FIG. 2 graphically illustrates the magnitudes of real and imaginary refractive-index components of rutile crystal as a function of wavelength;

FIG. 3 is a three-dimensional surface that graphically indicates the absorption cross-section of rutile spheres as a function of particle diameter and incident wavelength;

FIG. 4 illustrates the surface of FIG. 3 from a different perspective;

FIG. 5 shows three representative slices from the surface of FIGS. 3 and 4, graphically illustrating variation in absorption cross-section of rutile spheres as a function of wavelength for three specific sphere diameters;

FIG. 6 is a three-dimensional surface that graphically indicates the scattering cross-section of rutile spheres as a function of particle diameter and incident wavelength;

FIG. 7 shows three representative slices from the surface of FIG. 6, graphically illustrating variation in scattering cross-section of rutile spheres as a function of wavelength for three specific sphere diameters;

FIG. 8 is a three-dimensional surface that graphically indicates the extinction cross-section of rutile spheres as a function of particle diameter and incident wavelength;

FIG. 9 is a polar plot that graphically illustrates the angular distribution of scattered radiation from rutile spheres of various indicated diameters, wherein forward scatter is normalized to 1;

FIG. 10 graphically illustrates variation in real and imaginary refractive-index components of silicon across a range of wavelengths;

FIG. 11 is a three-dimensional surface that graphically indicates the absorption cross-section of silicon spheres as a function of particle diameter and incident wavelength;

FIG. 12 is a three-dimensional surface that graphically indicates the absorption cross-section of germanium spheres as a function of particle diameter and incident wavelength;

FIGS. 13 and 14 are representative slices from the surface of FIG. 12;

FIG. 15 graphically illustrates variation in real and imaginary refractive-index components of germanium across a range of wavelengths;

FIGS. 16–20 each show a three-dimensional surface that graphically indicates the absorption cross-section of silicon spheres, at an indicated constant value of the imaginary refractive-index component, as a function of particle diameter and incident wavelength;

FIG. 21 shows the relationship between a spherical particle's refractive index and a quantity F, which represents the ratio of the resonance wavelength to the particle radius.

FIG. 22 is a three-dimensional surface that graphically indicates the absorption cross-section of a nonabsorbing core of radius 0.1 μm, coated with a dye of 40 Å thickness, as a function of the index of refraction of the core material and incident wavelength; and FIG. 23 schematically illustrates an apparatus for producing uniformly sized particles in accordance with the present invention.

D. DETAILED DESCRIPTION OF THE PREFERRED EMBODIMENTS

The present invention relies on four mechanisms, which may be used in combination with one another, to produce composite media with sharp transitions between absorbed and unabsorbed spectral wavelength regions. These mechanisms are as follows.

1. Absorption-edge materials absorb radiation having wavelengths shorter than a characteristic minimum, which corresponds energetically to the magnitude of the material's electronic bandgap. Particle size has no significant effect on this property, although a narrow size distribution and an upper limit on average size may prove critical to ensure that the particles do not scatter radiation in the spectral region that is to remain transmissive. Useful bandgap materials include (but are not limited to) direct semiconductors, as described more fully below.

The bandgap necessarily varies with the choice of material, but can, in some instances, be shifted across a portion of the spectrum by varying the constituents of an alloy comprising a mix of bandgap materials. In particular, there exist many alloys of semiconductors whose compositions can be varied continuously. FIG. 1 illustrates this possibility for alloys of InN and GaN, which can be prepared over the full range of molar fractions for each constituent. A desired bandgap between that exhibited by pure InN or pure GaN can be obtained by combining the materials in the proportions indicated by the graph; relationships between bandgap and constituent mole fraction, such as that shown in FIG. 1, are generally smooth and can be straightforwardly determined by those skilled in the art without undue experimentation. Other useful alloy systems include those based on GaAs and AlAs.

2. Optical-resonance materials feature moderate intrinsic absorption, which would produce negligible overall absorption at the particle concentrations employed in the present invention. However, the optical-resonance phenomenon, based on self-reinforcing internal reflections, results in "absorption cross-sections" greater than unity in certain spectral regions; in other words, more radiation can be absorbed by the particle than actually falls geometrically on its maximum cross-sectional area. This is due to the wave nature of electromagnetic radiation and the propensity of the particle to "trap" certain frequencies of radiation, causing the radiation to travel back and forth within the particle until it is finally absorbed. The magnitude of the optical-resonance effect depends on the wavelength of incident radiation, the particle size, and the values of the real and imaginary components of the refractive index; particles that are large compared with the wavelength of incident radiation exhibit so many closely spaced (in terms of wavelength) resonances as to render selective absorption or scattering nearly impossible to control and use.

Optical resonance is enhanced by a high refractive index due to the resulting strong internal reflections, and also by a moderate intrinsic absorption level. Excessive absorption diminishes the resonance effect by immediately dissipating radiation as it enters the particle, while insufficient absorption causes incident radiation merely to undergo many reflections inside the particle; the radiation eventually leaves the particle without significant attenuation. Useful optical-resonance materials include (but are not limited to) "indirect" semiconductors, which exhibit gradual absorption edges, and whose overall absorption levels become significant only in resonant spectral regions.

In particular, preferred optical-resonance materials have refractive indices whose real components (N, as defined below) exceed 2; more preferably the index exceeds 3, and indices of 4 or 5 are even more advantageous. Preferred materials also exhibit only moderate absorption in the spectral region of interest. By "moderate absorption" we mean imaginary refractive-index components (K, as defined below) that range approximately from 0.02 to 0.5.

The following semiconductors are useful resonance absorbers:

| Chemical Formula | Name | $\lambda_{bandgap}$ (μm) |
| --- | --- | --- |
| AlP | Aluminum Phosphide | 0.506 |
| $Al_xIn_{(1-x)}P$ | Aluminum Indium Phosphide | 0.506–0.918 |
| AlAs | Aluminum Arsenide | 0.579 |
| AlSb | Aluminum Antimonide | 0.765 |
| $GaAs_xP_{(1-x)}$ | Gallium Arsenide Phosphide | 0.548–0.817 |
| GaSb | Gallium Antimonide | 1.77 |
| CdSe | Cadmium Selenide | 0.712 |
| CdTe | Cadmium Telluride | 0.861 |
| ZnTe | Zinc Telluride | 0.551 |
| Si | Silicon | 1.12 |
| Ge | Germanium | 1.907 |
| — | Alloys of Silicon and Germanium | 1.12–1.907 | where $\lambda_{bandgap}$ represents the ceiling absorption wavelength below which the material is suitable.

An effective absorption cross-section larger than the particles' true geometric cross-section results in the need for a proportionately smaller concentration of particles to produce a desired level of absorption, assuming even particle distribution. Using, as an example, rutile or $TiO_2$ particles of average diameter 0.075 μm and absorption cross-sections of 1.5, a typical working particle concentration (by volume) to produce 86.5% absorption is generally about 0.003%. Twice that concentration, or 0.006%, yields an absorption of 98.2%.

Small particles of bandgap materials will frequently exhibit resonance peaks as well as an absorption cutoff. Such resonance effects can greatly enhance the already-strong absorption at characteristic wavelengths near the energy bandgap of the absorption edge. Any selective absorption within the visible spectrum will create powerful, very pure colors.

3. Scattering. The milky appearance found in translucent substances is due to scattering of visible light. This sometimes-undesirable effect occurs as a result of material inhomogeneities, the presence of large particles, agglomerations of small particles highly concentrated in a carrier material, and/or mismatch between the refractive index of highly concentrated particles and that of the carrier material.

The present invention exploits, for certain applications, the particle size- and wavelength-dependent scattering properties (with regard to incident radiation) of select particulate materials to achieve scattering of certain shorter wavelengths without scattering longer-wavelength radiation, thereby permitting its unobstructed transmission and avoiding, for example, a milky appearance.

4. Refraction Index Mismatch. Coating an inorganic, optically resonant core particle of suitable dielectric constant with an inorganic radiation-absorptive material can, at matching wavelengths, transform the core particle into a composite structure whose color intensity exceeds that of the dye alone. This effect arises through excitation of the dye by the evanescent (transient) wave that runs around the resonant particle outside its physical dimension. To maximize the absorption cross-section and, therefore, the intensity of the evanescent wave, the refractive indices of the particle and that of the surrounding shell are deliberately mismatched, resulting in substantial trapping of incident light within the core particle and delivery of energy to the surrounding shell through the evanescent wave.

The selection of particles suited for achieving particular optical properties such as transmissivity or color is aided by Mie theory of light scattering, which can be used to establish, for a given type and size of particle, the degree to which a particle scatters and/or absorbs radiation of particular wavelengths. The ability to prevent transmission in certain wavelength bands—that is, the particle's net resistance to transmission of target radiation—is called "extinction," and results both from absorption and scattering of such radiation. Extinction can be controlled through the choice of particle material, its size and shape, and the characteristics of the surrounding medium.

For an x-polarized electromagnetic wave incident in the z-direction on a spherical particle, the scattered amplitudes (in the limit of large distances from the sphere) can be represented as:

$E_{s\theta} = E_0 \, (-e^{ikr}/ikr) \, \cos\phi \, S_2(\cos\theta)$ $E_{s\phi} = E_0 \, (-e^{ikr}/ikr) \, \sin\phi \, S_1(\cos\theta)$ In the above equations, $E_{s\theta}$ and $E_{s\phi}$ are the amplitudes of the scattered E fields polarized in the $\theta$ or $\phi$ directions in a conventional spherical coordinate system. These two E field directions refer also to polarizations "in" and "perpendicular" to the plane of scattering. $E_0$ is the amplitude of the incident E field; k is the propagation vector in the surrounding medium with value $2\pi/\lambda$, where $\lambda$ is the wavelength of the radiation in the medium; and $S_1$ and $S_2$ are the scattering functions given by:

$$S_1 = \sum_n \frac{2n+1}{n(n+1)} (a_n \pi_n + b_n \tau_n)$$

$$S_2 = \sum_n \frac{2n+1}{n(n+1)} (a_n \tau_n + b_n \pi_n)$$

in which n is a summation index that is carried high enough to obtain convergence of the series (300 generally being sufficiently high for practical purposes). $\pi_n$ and $\tau_n$ are angle-dependent functions closely related to spherical harmonics, and are as follows:

$$\pi_n = \frac{P_n^1(\cos\theta)}{\sin\theta}$$

$$\tau_n = \frac{dP_n^1(\cos\theta)}{d\theta}$$

where $P_n^1(\cos\theta)$ represents spherical harmonics of order n. The functions $a_n$ and $b_n$ are as follows:

$$a_n = \frac{m\psi_n(mx)\,\psi'_n(x) - \psi_n(x)\,\psi'_n(mx)}{m\psi_n(mx)\,\xi'_n(x) - \xi_n(x)\,\psi'_n(mx)}$$

$$b_n = \frac{\psi_n(mx)\,\psi'_n(x) - m\psi_n(x)\,\psi'_n(mx)}{\psi_n(mx)\,\xi'_n(x) - m\xi_n(x)\,\psi'_n(mx)}$$

where $x = ka = 2\pi N_{med} a/\lambda$, where $N_{med}$ is the refractive index of the surrounding medium, a is the radius of the particle sphere, $\lambda$ is the vacuum wavelength of the incident radiation, and $m = N_1/N_{med}$, where $N_1$ is the usually complex index of refraction of the scattering sphere. The complex and real components of $N_1$ are typically represented as $N_1 = N + iK$, where K is proportional to the absorption coefficient. Plots of N and K as a function of wavelength for rutile crystals appear in FIG. 2. The functions $\psi$ and $\xi$ are defined as:

$$\psi_n(\rho) = (\pi\rho/2)^{1/2} J_{n+\frac{1}{2}}(\rho)$$

$$\xi_n(\rho) = (\pi\rho/2)^{1/2} (J_{n+\frac{1}{2}}(\rho) + iY_{n+\frac{1}{2}}(\rho))$$

where J and Y refer to the half-integer Bessel and Neumann functions.

The foregoing equations can be used to calculate the degree of scattering and absorption for a given particle. The total scattering cross-section of a particle is derived by integration of the scattered light over the solid angle $4\pi$. The extinction cross-section, which represents the sum of absorption and scattering, can be similarly calculated; for the unpolarized light found in ordinary environments, one averages over all polarizations to derive values for scattering and extinction cross-sections as follows:

$$C_{sca} = \frac{2\pi}{k^2} \sum_n (2n+1)(|a_n|^2 + |b_n|^2)$$

$$C_{ext} = \frac{2\pi}{k^2} \sum_n (2n+1) Re(a_n + b_n)$$

The absorption cross-section, $C_{abs}$, is the difference between the extinction and scattering cross-sections.

The following computer program, written in FORTRAN and based on the foregoing equations, may be used to calculate scattering and extinction cross-sections, the scattering matrix elements and the angular dependence of the scattered light as a function of sphere radius, the complex index of refraction $N_1$, the refractive index of the surrounding medium, and the wavelength of incident radiation.

```
1       PROGRAM MIE
2  C
3  C------------------------------------
4  C
5  C
6  C
7  C
8  C
9  C
10 C
11 C
12 C------------------------------------
13      IMPLICIT REAL*8 (A-H,O-Z)
14      COMPLEX*16 REFREL,S1(200),S2(200)
15      WRITE (5,11)
16 C------------------------------------
17 C    INSERT HERE REFMED (REAL INDEX OF THE SURROUNDING MEDIUM)
18 C------------------------------------
16      REFMED--1.0D0
20 C------------------------------------
21 C    REFRACTIVE INDEX OF SPHERE= REFRE+I*REFIM
22 C------------------------------------
23      REFRE=1.55D0
24         REFIM=0.D0
25      REFREL=DCMPLX(REFRE,REFIM)/REFMED
26      WRITE(5,12) REFMED,REFRE,REFIM
27 C------------------------------------
28 C    SPHERE RADIUS AND WAVELENGTH OF LIGHT IN SAME UNITS ( MICRONS)
29 C------------------------------------
30      RAD=.525D0
31      WAVEL=.6328D0
32      X=2.*3.141592654*RAD*REMED/WAVEL
33      WRITE(5,13) RAD,WAVEI
34      WRITE(5,14) X
35 C------------------------------------
36 C    NANG=NUMBER OF ANGLES BETWEEN 0 AND 90 DEGREES AT WHICH SCATTERING
37 C    MATRIX ELEMENTS WILL BE CALCULATED
38 C------------------------------------
39      NANG=11
```

```
40        DANG=1.570796327/DFLOAT(NANG-1.)
41        CALL BHMIE(X,REFREL,NANG,S1,S2,QEXT,QSCA,QBACK)
42        WRITE(5,65) QSCA,QEXT,QBACK
43        WRITE(5,17)
44 C-----------------------------------------------------------------
45 C  S11 NORMALIZED TO ONE IN FORWARD DIRECTION. S33 AND S34 NORMALIZED
46 C  BY S11. POL= DEGREE OF POLARIZED LIGHT WHEN INCIDENT UNPOLARIZED
47 C-----------------------------------------------------------------
48        S11NOR=.5*(CDABS(S2(1))**2+CDABS(S1(1))**2)
49        NAN=2*NANG-1
50        DO 355 J=1,NAN
51        AJ=J
52        S11=0.5*CDABS(S2(J))*CDABS(S2(J))
53        S11=S11+.5*CDABS(S1(J))*CDABS(S1(J))
54        S12=.5*CDABS(S2(J))*CDABS(S2(J))
55        S12=S12-.5CDABS(S1(J))*CDABS(S1(J))
56        POL=-S12/S11
57        S33=DREAL(S2(J)*DCONJG(S1(J)))
58        S33=S33/S11
59        S34=DIMAG(S2(J)*DCONJG(S1(J)))
60        S34=S34/S11
61        S11=S11/S11NOR
62        ANG=DANG*(AJ-1.)*57.29577951
63    355 WRITE(5,75) ANG,S11,POL,S33,S34
64     65 FORMAT (//,1X,'QSCA= ',E13.6,3X,'QEXT= ',E13.6,3X,
65       &'QBACK= ',E13.6)
66     75 FORMAT(1X,F6.2,2X,E13.6,2X,E13.6,2X,E13.6,2X,E13.6)
67     11 FORMAT (/'SPHERE SCATTERING PROGRAM'//)
68     12 FORMAT (5X,'REFMED= ',F8.4,3X,'REFRE= ',E14.6,3X,
69       &'REFIM= ',E14.6)
70     13 FORMAT(5X,'SPHERE RADIUS= 'F7.3,3X,'WAVELENGTH= 'F7.4)
71     14 FORMAT(5X, 'SIZE PARAMETER= ',F8.3/),
72     17 FORMAT(//,2X, 'ANGLE',7X,'S11',13X,'POL',13X,'S33',13X,'S34'//)
73        STOP
74        END
75 C-----------------------------------------------------------------
76 C  SUBROUTINE CALCULATES SCATTERING MATRIX ELEMENTS, SCATTERING AND
77 C  EXTINCTION CROSS-SECTIONS
78 C-----------------------------------------------------------------
79        SUBROUTINE BHMIE(X,REFREL,NANG,S1,S2,QEXT,QSCA,QBACK)
80        IMPLICIT REAL*B (A-H,O-Z)
67     11 FORMAT (/'SPHERE SCATTERING PROGRAM'//)
68     12 FORMAT (6X,'REFMED= ',F8.4,3X,'REFRE= ',E14.6,3X,
69       &'REFIM= ',E14.6)
70     13 FORMAT(5X,'SPHERE RADIUS= 'F7.3,3X,'WAVELENGTH= 'F7.4)
71     14 FORMAT(5X, 'SIZE PARAMETER= ',F8.3/)
72     17 FORMAT(//,2X,'ANGLE',7X,'S11',13X,'POL',13X,'S33',13X,'S34'//)
73        STOP
74        END
75 C-----------------------------------------------------------------
76 C  SUBROUTINE CALCULATES SCATTERING MATRIX ELEMENTS, SCATTERING AND
77 C  EXTINCTION CROSS-SECTIONS
78 C-----------------------------------------------------------------
79        SUBROUTINE BHMIE(X,REFREL,NANG,S1,S2,QEXT,QSCA,QBACK)
80        IMPLICIT REAL*8 (A-H,O-Z)
81        DIMENSION AMU(100),THETA(100),PI(100),TAU(100),PIO(100),PI1(100)
82        COMPLEX*16 D(3000),Y,REFREL,XI,XI0,XI1,AN,BN,S1(200),S2(200)
83        DX=X
84        Y=X*REFREL
85 C-----------------------------------------
86 C  SERIES TERMINATED AFTER NSTOP TERMS
87 C-----------------------------------------
88        XSTOP=X+4.*X**.3333+2.
89        NSTOP=XSTOP
90        YMOD=CDABS(Y)
91        NMX=DMAX1(XSTOP,YMOD) + 15
92        DANG=1.570796327/DFLOAT(NANG-1)
93        DO 525 J=1,NANG
94        THETA(J)=(DFLOAT(J)-1.)*DANG
95    555 AMU(J)=DCOS(THETA(J))
96 C-----------------------------------------------------------------
97 C  LOGARITHMIC DERIVATIVE D(J) CALCULATED BY DOWNWARD RECURRENCE
98 C  BEGINNING WITH INITIAL VALUE 0.0+ 1.0*I AT J=NMX
99 C-----------------------------------------------------------------
100       D(NMX)=DCMPLX(0.D0,0.D0)
101       NN=NMX-1
102       DO 120 N=1,NN
103       RN=NMX-N+1
104   120 D(NMX-N)=(RN/Y)-(1./(D(NMX-N+1)+RN/Y))
105       DO 666 J=1,NANG
```

```
106        PIO(J)=0.D0
107   666  PI1(J)=1.D0
108        NN=2*NANG-1
109        DO 777 J=1,NN
110        S1(J)=DCMPLX(0.D0,0.D0)
111   777  S2(J)=DCMPLX(0.D0,0.D0)
112   C--------------------------------------------------------
113   C    RICCATI BESSEL FUNCTIONS WITH REAL ARGUMENT 8 CALCULATED
114   C    BY UPWARD RECURRENCE
115   C--------------------------------------------------------
116        PSI0=DCOS(DX)
117        PSI1=DSIN(X)
118        CHI0=-DSIN(X)
119        CHI1=DCOS(DX)
120        APSI0=PSI0
121        APSI1=PSI1
122        XI0=DCMPLX(APSI0,-CHI0)
123        XI1=DCMPLX(APSI1,-CHI1)
124        QSCA=0.D0
125        N=1
126   200  DN=N
127        RN=N
128        FN=(2.*RN+1.)/(RN*(RN+1.))
129        PSI=(2.*DN-1.)*PSI1/DX-PSI0
130        APSI=PSI
131        CHI=(2.*RN-1.)*CHI1/X-CHI0
132        XI=DCMPLX(APSI,-CHI)
133        AN=(D(N)/REFREL+RN/X)*APSI-APSI1
134        AN=AN/((D(N)/REFREL+RN/X)*XI-XI1)
135        BN=(REFREL*D(N)+RN/X)*APSI-APSI1
136        BN=BN/((REFREL*D(N)+RN/X)*XI-XI1)
137        QSCA=QSCA+(2.*RN+1.)*(CDABS(AN)*CDABS(AN)+CDABS(BN)*CDABS(BN))
138        DO 789 J=1,NANG
139        JJ=2.*NANG-J
140        PI(J)=PI1(J)
141        TAU(J)=RN*AMU(J)*PI(J)-(RN+1.)*PIO(J)
142        P=(-1)**(N-1)
143        S1(J)=S1(J)+FN*(AN*PI(J)+BN*TAU(J))
144        T=(-1)**N
145        S2(J)=S2(J)+FN*(AN*TAU(J)+BN*PI(J))
146        IF(J.EQ.JJ) GOTO 789
147        S1(JJ)=S1(JJ)+FN*(AN*PI(J)*P+BN*TAU(J)*T)
148        S2(JJ)=S2(JJ)+FN*(AN*TAU(J)*T+BN*PI(J)*P)
149   789  CONTINUE
150        PSI0=PSI1
151        PSI1=PSI
152        APSI1=PSI1
153        CHI0=CHI1
154        CHI1=CHI
155        XI1=DCMPLX(APSI1,-CHI1)
156        N=N+1
157        RN=N
158        DO 999 J=1,NANG
159        PI1(J)=((2.*RN-1.)/(RN-1.))*AMU(J)*PI(J)
160        PI1(J)=PI1(J)-RN*PIO(J)/(RN-1.)
161   999  PIO(J)=PI(J)
162        IF(N-1-NSTOP) 200,300,300
163   300  QSCA=(2./(X*X))*QSCA
164        QEXT=(4./(X*X))*QSCA
165        QBACK=(4./(X*X))*CDABS(S1(2*NANG-1))*CDABS(S1(2*NANG-1))
166        RETURN
167        END
``` a. Blocking Applications

Figure 2:
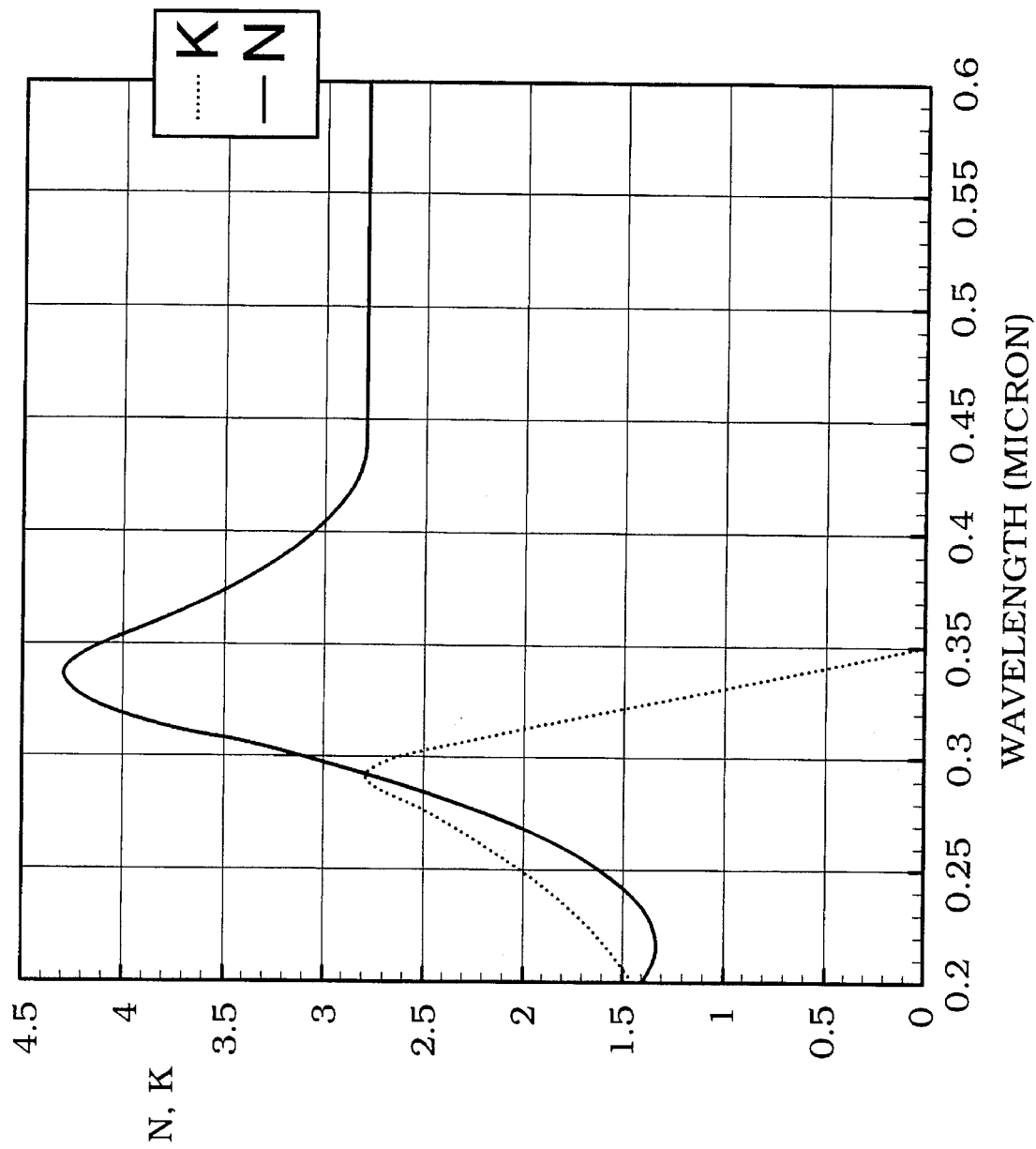
Figure 3:
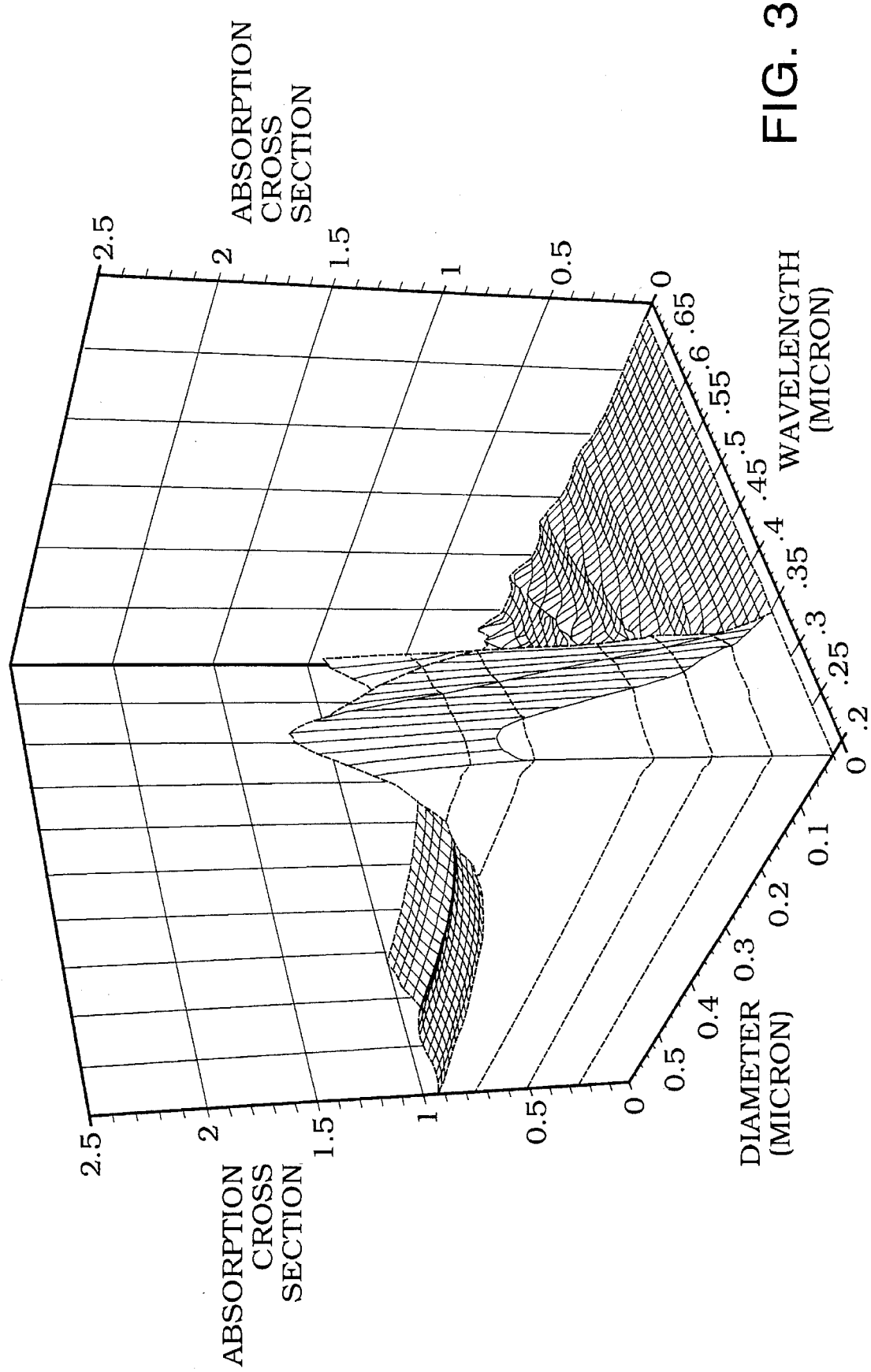
Figure 4:
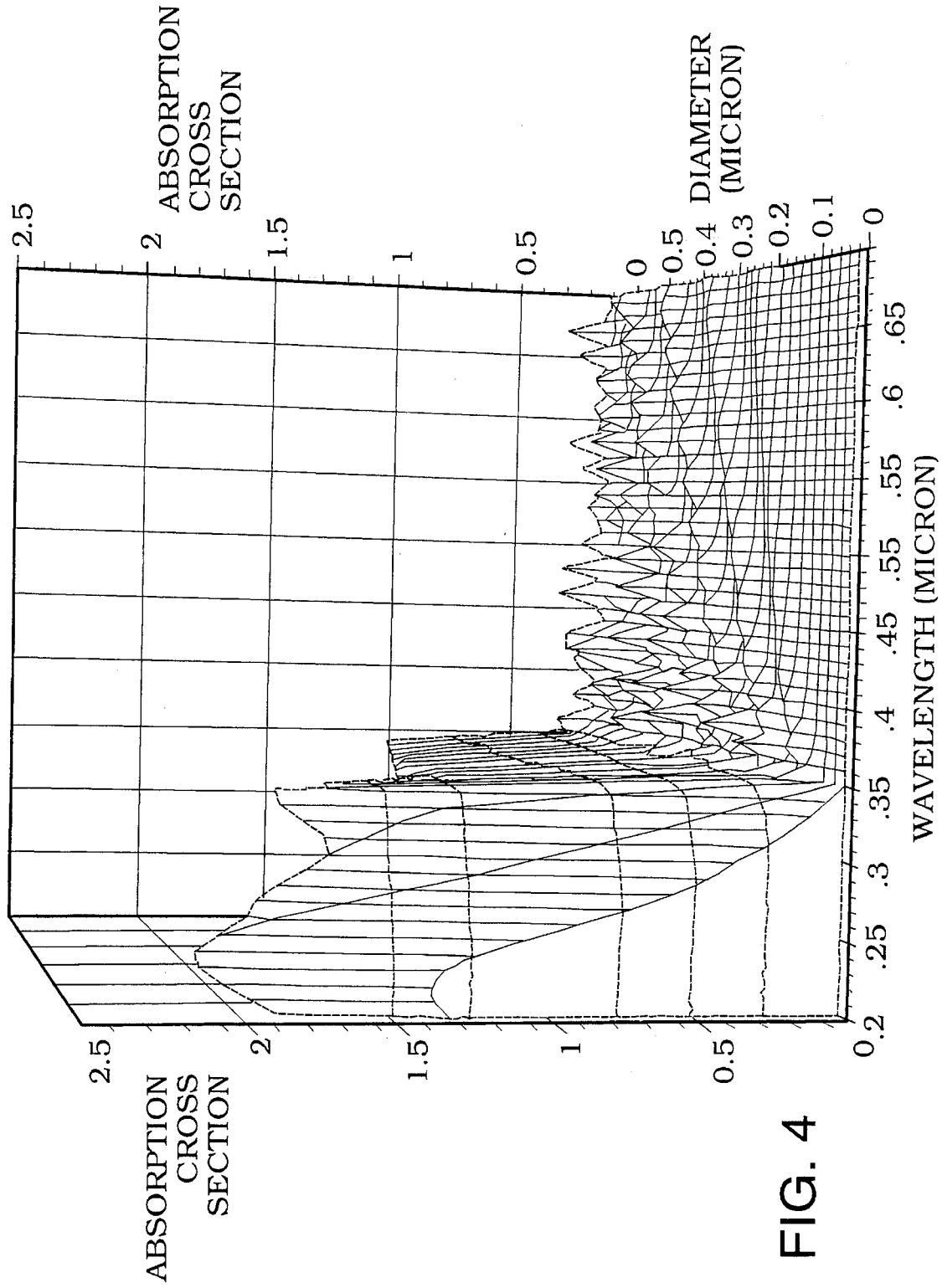

As a representative example, consider the ultraviolet (UV) blocking properties of small crystalline particles of titania ($TiO_2$) having the rutile crystalline structure. Because rutile crystals absorb only radiation with wavelengths below 0.36 µm, the index of refraction is complex below 0.36 µm. Furthermore, rutile crystals are optically anisotropic, since the structure is noncubic; however, because the particles will have a random crystallographic orientation within the host material, this condition can be simplified for purposes of calculation (without significant deviation from experimental observation) by averaging over the refractive indices in the various directions. FIG. 2 illustrates the variation of the averaged refractive index of rutile crystal with incident wavelength. In the calculations a refractive index of 1.33, representative of water and a number of common materials, is ordinarily assumed for the surrounding carrier medium.

Particles of rutile titania are dispersed in an otherwise clear container material such as glass, polyethylene or polypropylene to absorb and scatter UV radiation while retaining good transparency in the visible region. The absorption, extinction and scattering cross-sections of titania spheres, as a function of particle size and wavelength of incident radiation, appear in FIGS. 3-8, where the cross-section value relates the effective cross-section to the particle's geometric cross-section (i.e., the area the particle presents to incident radiation). Effective absorption cross-sections greater than 1 result from optical resonance phenomena. The extinction cross-section, which represents the sum of absorption and scattering cross-sections, exhibits the largest maximum values.

Figure 9:
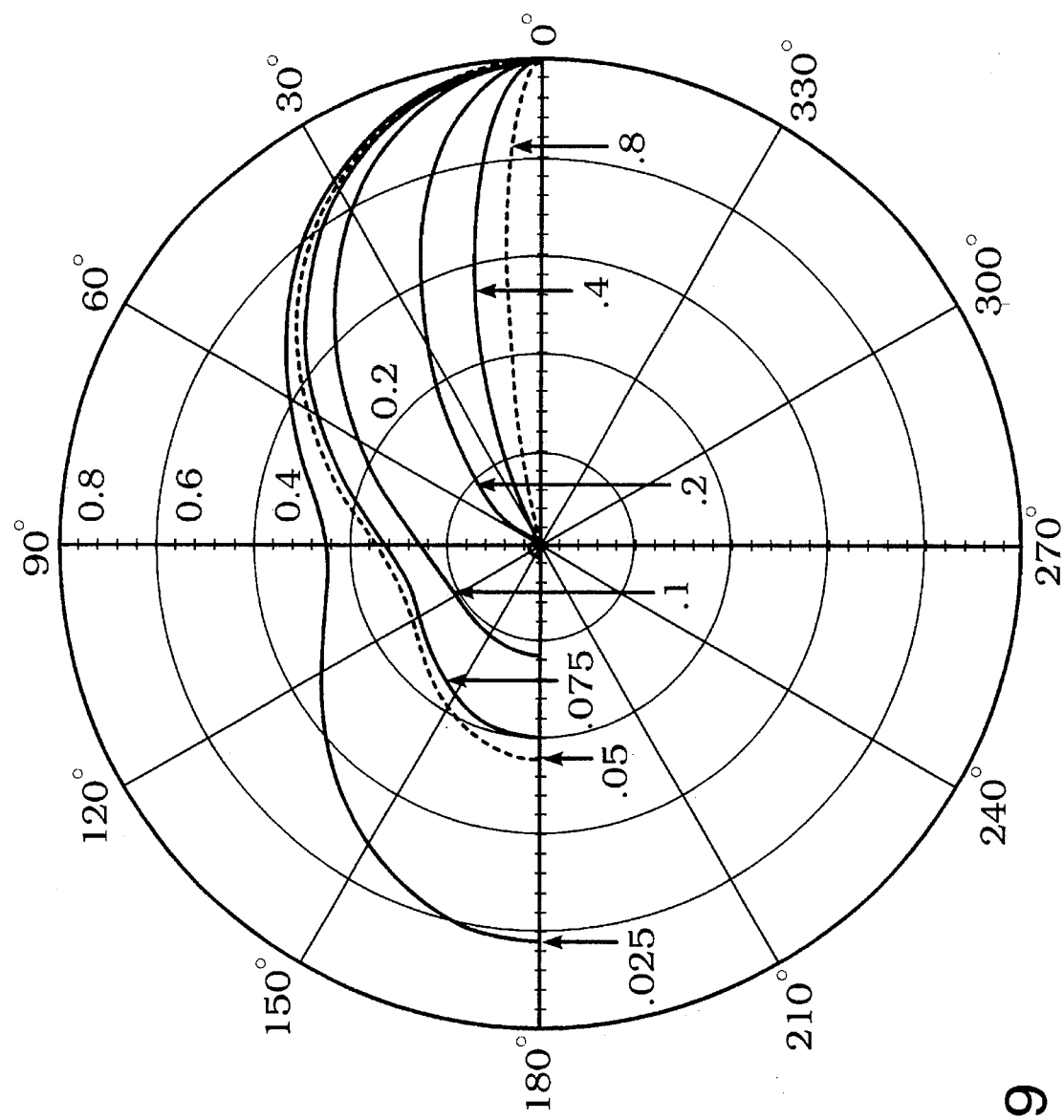

However, only that scattering which results in a diminished or nonexistent directional component toward the interior of the container assists in the blockage of incident radiation. Thus, an important practical issue for purposes of determining the effectiveness of the particle is the degree of angular deflection that results from scattering. The angular distribution of the scattered radiation is illustrated in FIG. 9 for rutile spheres of varying diameters at an incident wavelength of 0.33 μm. The polar diagram assumes that incident radiation comes from the left, along the 180° axis. Forward-scattered (i.e., undisturbed) radiation exits along the 0° axis, and has been normalized to unity in accordance with standard convention.

Figure 5:
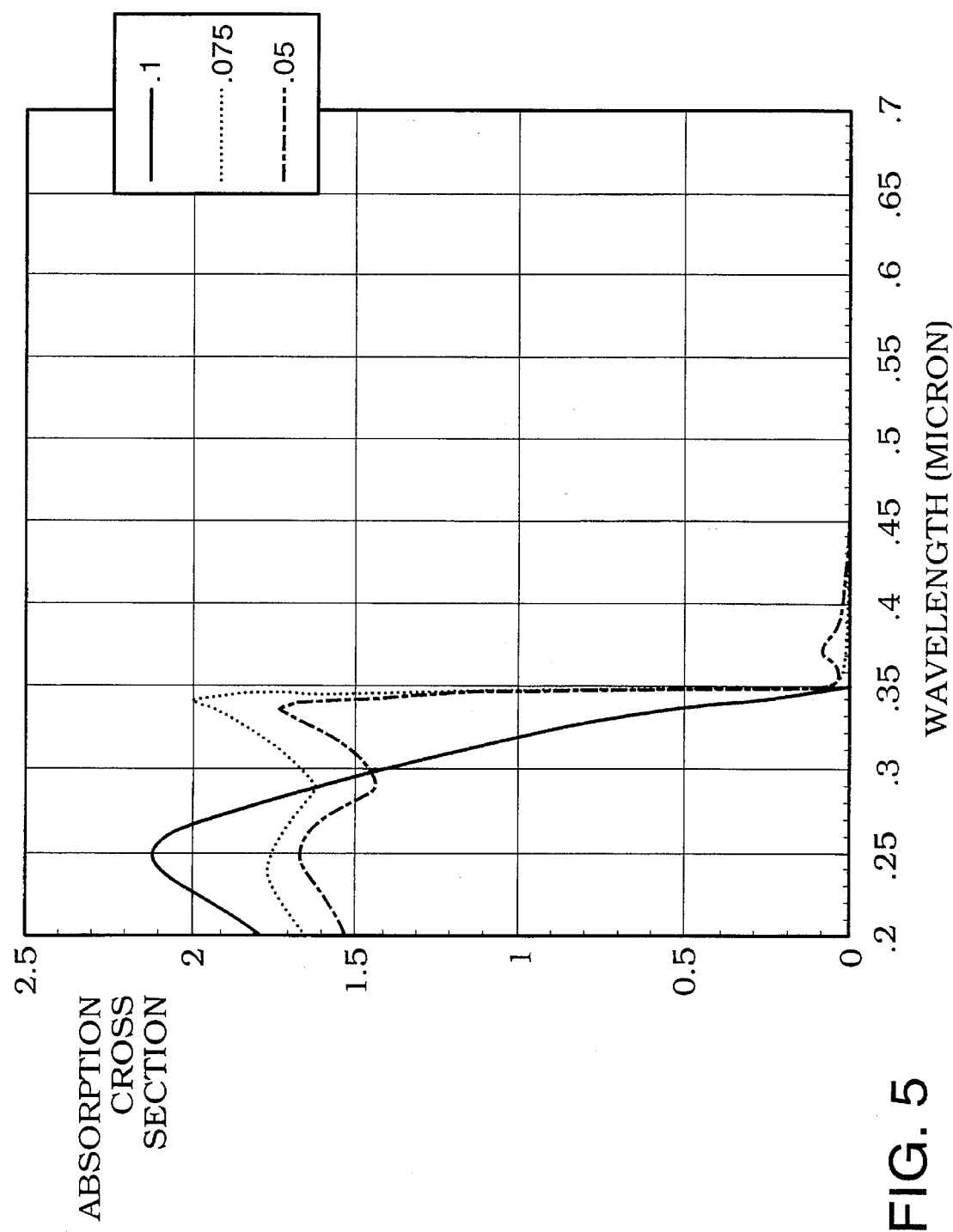
Figure 6:
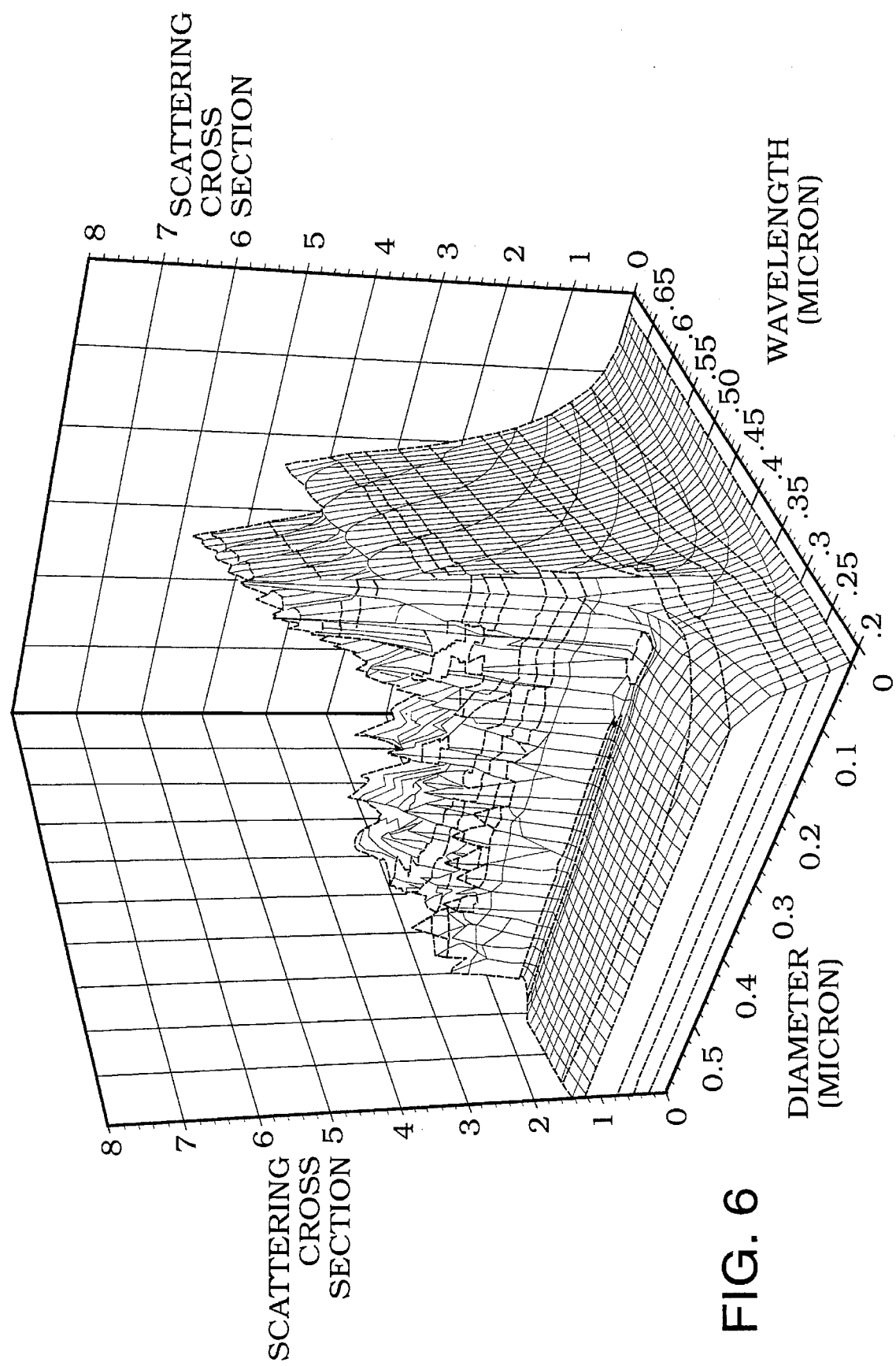
Figure 7:
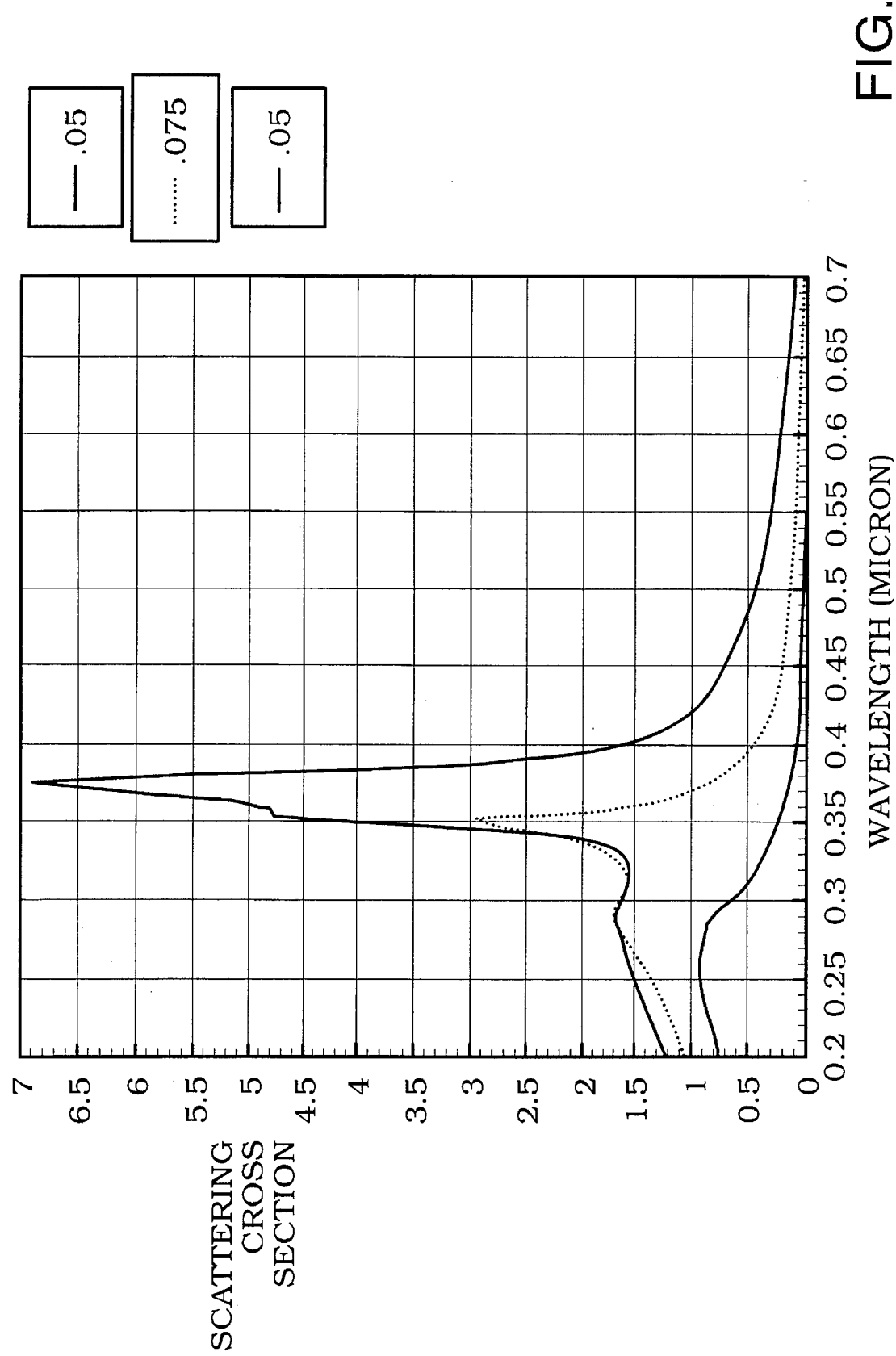
Figure 8:
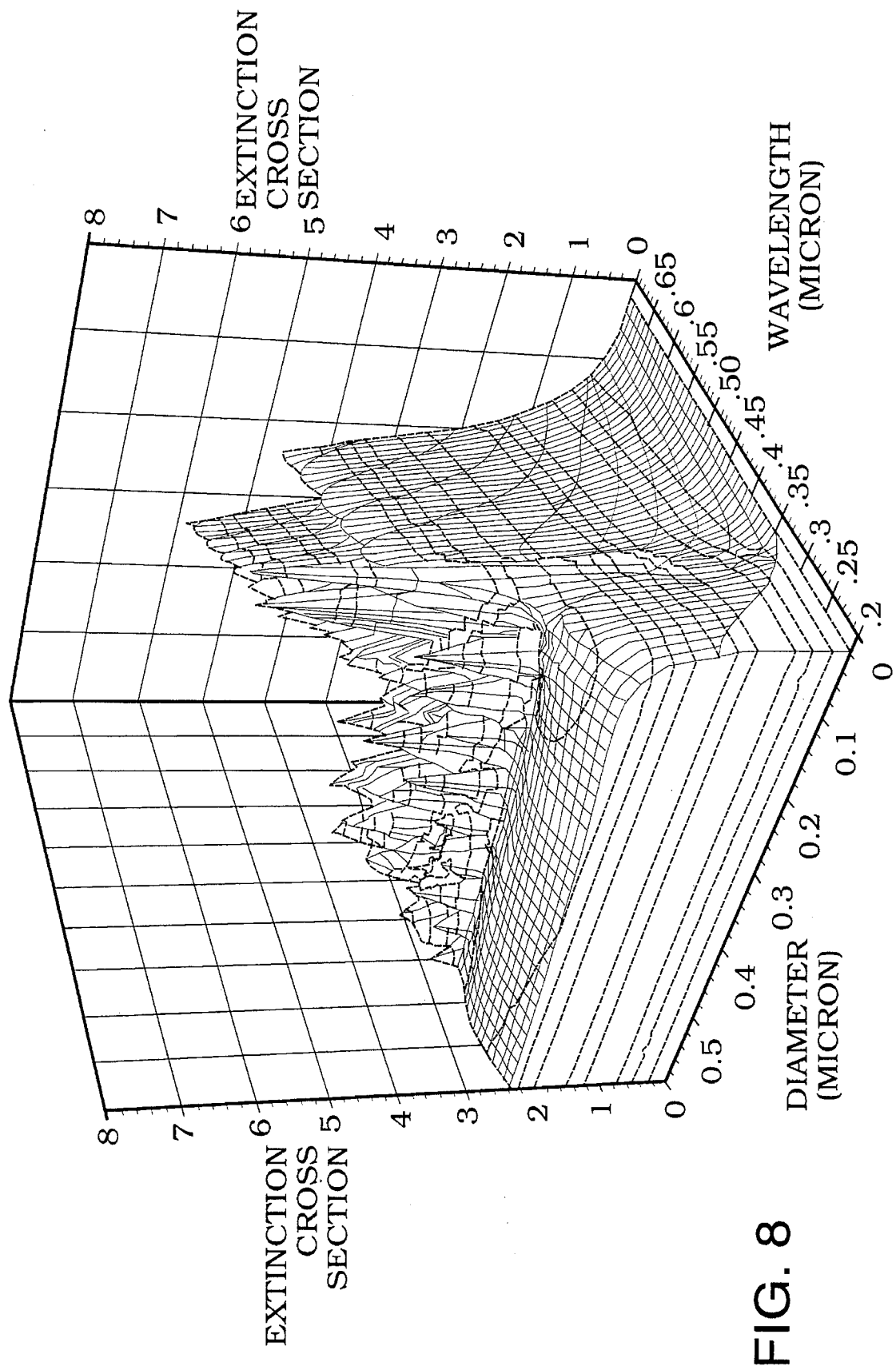

FIG. 9 demonstrates that particle size, relative to the wavelength of incident radiation, determines the degree of non-forward scattering. As shown in the figure, particles with diameters larger than 0.1 μm scatter primarily in the forward direction. To obtain scattering in directions away from, for example, the interior of a container, it is necessary to use rutile particles smaller than 0.1 μm. However, as indicated in FIGS. 5 and 7, too small a particle simply does not absorb or scatter to a large extent; therefore even a significant non-forward scattering component cannot compensate for the particle's overall performance limitations.

In view of the foregoing, preferred rutile particles have diameters of approximately 0.075 μm, which represents an optimal compromise between high absolute scattering and absorbance levels, on one hand, and high levels of non-forward scattering on the other. Particles having a distribution of diameters, centering on 0.075 μm but ranging from 0.05 μm to 0.1 μm, may be more easily manufactured and will also perform satisfactorily. For these diameters, significant absorption of UV radiation is achieved while scatter in the visible region (i.e., wavelengths between 0.4 and 0.7 μm) is acceptably small; accordingly, when incorporated into a container, the particles will not generate a milky appearance.

The concentration of particles necessary for a given application depends on the desired degree of opacity to target radiation, and the absorption and scattering cross-sections of the particles. For practical purposes, we have found it useful to focus primarily on the particles' absorption cross-section and employ a sufficient concentration of particles to provide complete effective area coverage.

Considering only absorption cross-sections, denoted by S, each particle of radius r effectively covers an area $\pi r^2 S$. Accordingly, the number of particles N per unit volume necessary to achieve complete effective area coverage in a wall of thickness δ and area α is given by $N=\alpha/\delta\pi r^2 S$. Using the above spherical rutile example and assuming uniform particle diameters of 0.075 μm, FIG. 5 reveals an average absorption cross-section S of about 1.5 below wavelengths of 0.4 μm. Thus, the necessary volumetric density of particles is approximately $1.5 \times 10^{11}$ particles/cm$^3$; the total volume fraction of particles is given by $4\pi r^3 N/3 = 4r\alpha/3\delta S$, or $3.3 \times 10^{-5}$, in percentage volume terms about 0.003%. The foregoing equation indicates that the smallest volume of needed particles is obtained through choice of the smallest acceptable particle radius. For a typical blocking application, a volume fraction 0.003% represents an attractively small cost component.

Alternatively, particles having a bandgap (i.e., absorption edge) corresponding to a desired numerical wavelength cutoff value also provide advantageous blocking performance. These are dispersed within a suitable container material, such as plastic, at a sufficient volumetric density to effectively cover the area of the container, thereby preventing transmission of wavelengths shorter than cutoff value. In this simple case, a distribution of particle sizes can be employed, since absorption depends primarily on the nature of the bandgap material rather than its geometry or size. However, to prevent unwanted scattering in the visible region, the Mie calculations can be used to ascertain a maximum particle size, as described above.

In addition to possessing a bandgap of the correct energy, preferred materials also exhibit strong absolute absorption levels. This property arises from quantum mechanically allowed optical transitions from the valence band to the conduction band, and is exhibited by so-called "direct" semiconductors where the bottom of the conduction band and the top of the valence band occur at the center of the Brillouin zone. In this zone, electronic transitions occur without change in the wave-propagation vector k, the transitions going from k=0 to k=0 at the absorption edge. Direct semiconductors include ZnO, GaN, $Ga_xIn_{1-x}N$ over all values of x, and GaAs.

For example, to block UV radiation beginning at a wavelength of 0.4 μm, particles having a bandgap of 3.1 eV or less may be employed; suitable examples of such materials include ZnO and GaN, both of which are direct semiconductors. To keep foodstuffs such as milk in long-term storage without deterioration, not only UV radiation but also visible light in the blue and green regions must be excluded. In this case control agents having a bandgap of 2.4 eV or less may be used; a suitable example is $Ga_xIn_{1-x}N$ where x=0.4. (For applications involving foodstuffs and biological substances where toxicity cannot be tolerated, otherwise suitable materials such as alloys containing GaAs cannot be utilized.)

Alternatively, one can employ particles that exhibit optical resonance across the spectrum of wavelengths to be excluded; in this case, since a range of wavelengths is being blocked, the volumetric density is typically determined by reference to the smallest absorption cross-section within the range. Silicon spheres with radii ranging from 0.03 μm to 0.07 μm satisfactorily block visible light beginning in the green region and extending into the UV range. Titanium dioxide spheres of radius 0.075 μm satisfactorily block UV radiation in the UVA, UVB and UVC spectral regions.

Figure 13:
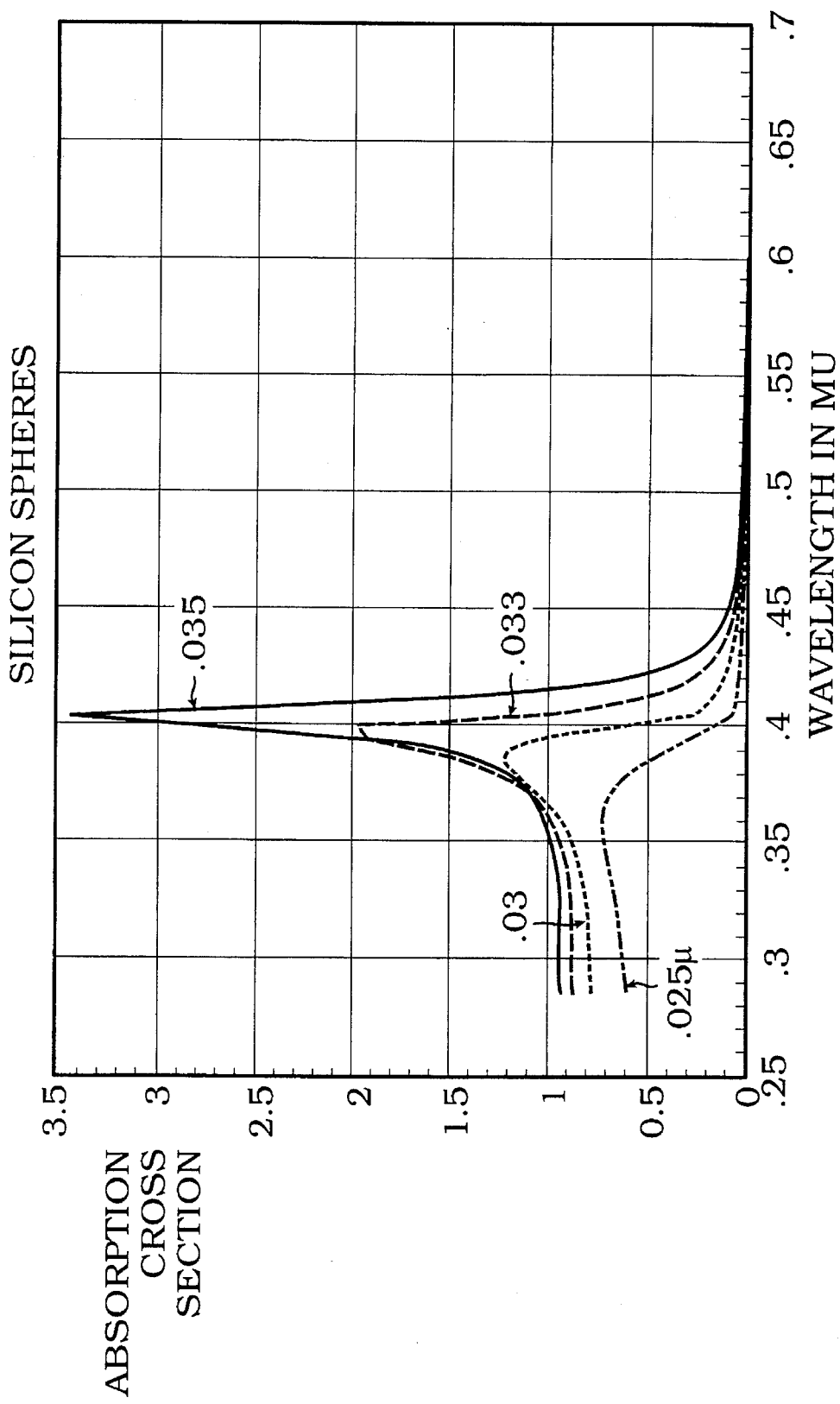

Indeed, silicon spheres can be used to block UV radiation over a broad spectrum. FIG. 13 illustrates use of the Mie calculations to derive absorption cross-sections for silicon extending beyond the visible region deep into the UV. As revealed in the figure, particles having a radius of 0.035 μm exhibit a sharp resonance absorption at a wavelength of 0.41 μm, while absorption in the visible region is slight. In the UV region the absorption cross-section never falls substantially below 1, since the value of K is now large (i.e., 0.5 and greater); however, an absorption cross-section of 1 is quite usable for practical purposes.

Figure 14:
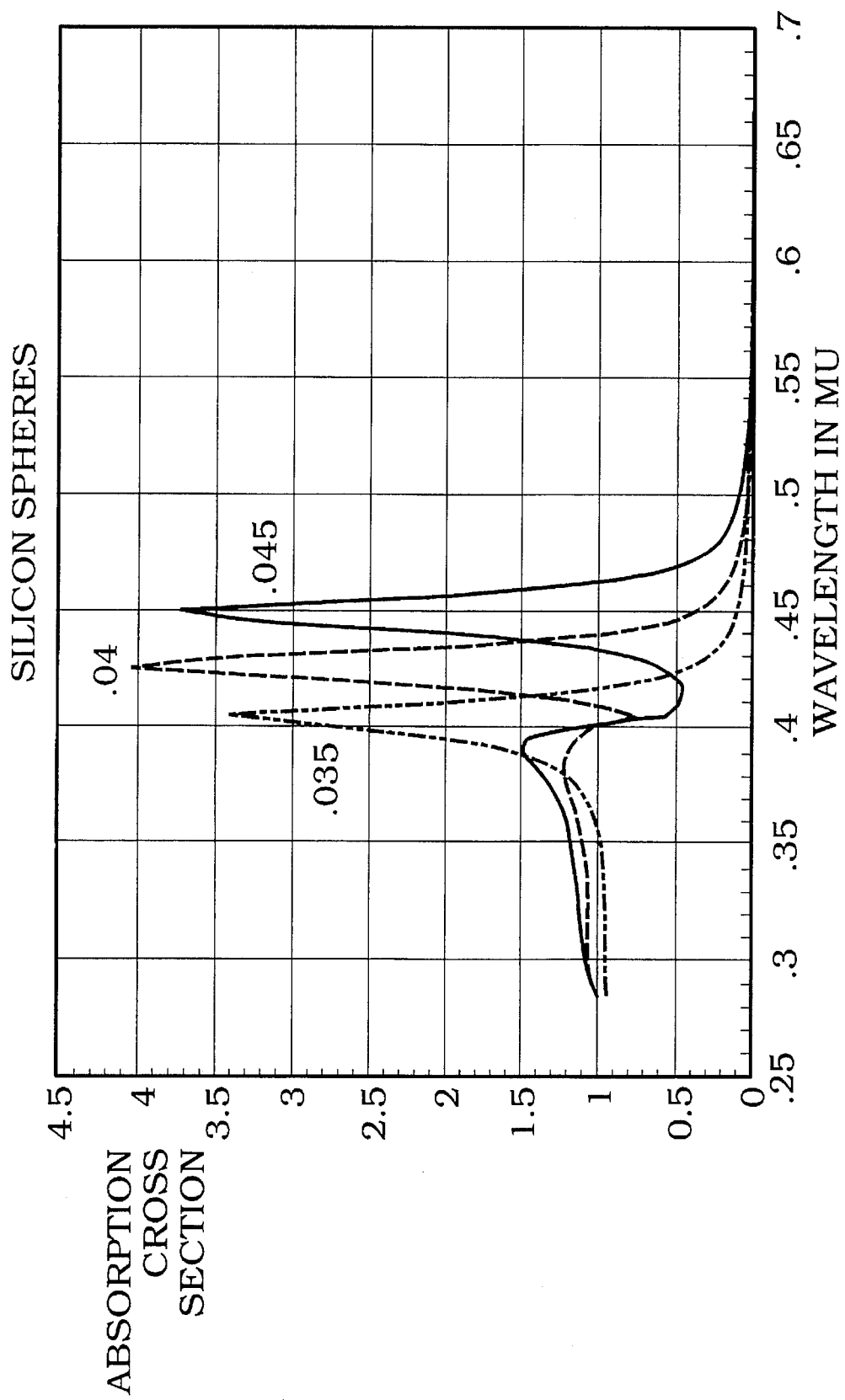

Even smaller particles (e.g., of radii 0.033 and 0.03 μm, as shown in FIG. 13) exhibit absorption cross-sections of useful values in the UV region. Thus, for broad-band UV blockage, silicon spheres of radii ranging from 0.03 μm to 0.035 μm, and perhaps as small as 0.025 μm, can be used advantageously. By extending the particle size from 0.045 μm to 0.3 μm, a portion of the blue spectrum can also be eliminated as shown in FIG. 14. Obviously, those skilled in the art will readily appreciate the manner in which these examples can be extended into other wavelength regions.

b. Inks and Paints

Particles with strong, wavelength-specific absorption properties make excellent pigments for use in ink and paint compositions. Suitable particulate materials exhibit pronounced optical resonances at selected frequencies in the visible spectrum. Such materials typically have high indices of refraction (resulting, as noted above, in the self-reinforced internal reflections characteristic of optical resonance) and moderate intrinsic absorption levels. Many common semiconductors, particularly indirect semiconductors, have absorption coefficients of desirable magnitudes. Suitable materials include silicon, germanium, alloys of silicon and germanium, GaP, GaAs, AlSb, and alloys of GaAs and AlAs; GaN and InN.

The absorption of a semiconductor can be increased by doping. In the case of a Group IV material such as silicon or germanium, suitable dopants include p-type conduction carriers from Group III (boron, aluminum, gallium, indium) and n-type carriers from Group V (phosphorus, arsenic, antimony). In the case of compounds or alloys based on elements from Groups III and V (e.g., GaAs), suitable p-type dopants are drawn from Group II (beryllium, magnesium, calcium, strontium, barium) and suitable n-type dopants from Group VI (oxygen, sulfur, selenium, tellurium). In order to obtain a meaningful increase in absorption, useful doping concentrations frequently approach the limit of solid solubility, or about $10^{20}$ to $10^{21}$ atoms/cm$^3$. For example, a dopant concentration of $10^{21}$ atoms/cm$^3$, or about 0.1% by weight, will increase the refractive-index component K by about 0.1. Furthermore, since the absorption due to the dopant (the so-called "free-carrier absorption") is proportional to the square of the incident wavelength, this absorption increases by a factor of about 3 across the visible spectrum, with the strongest absorptions in the red region.

Figure 10:
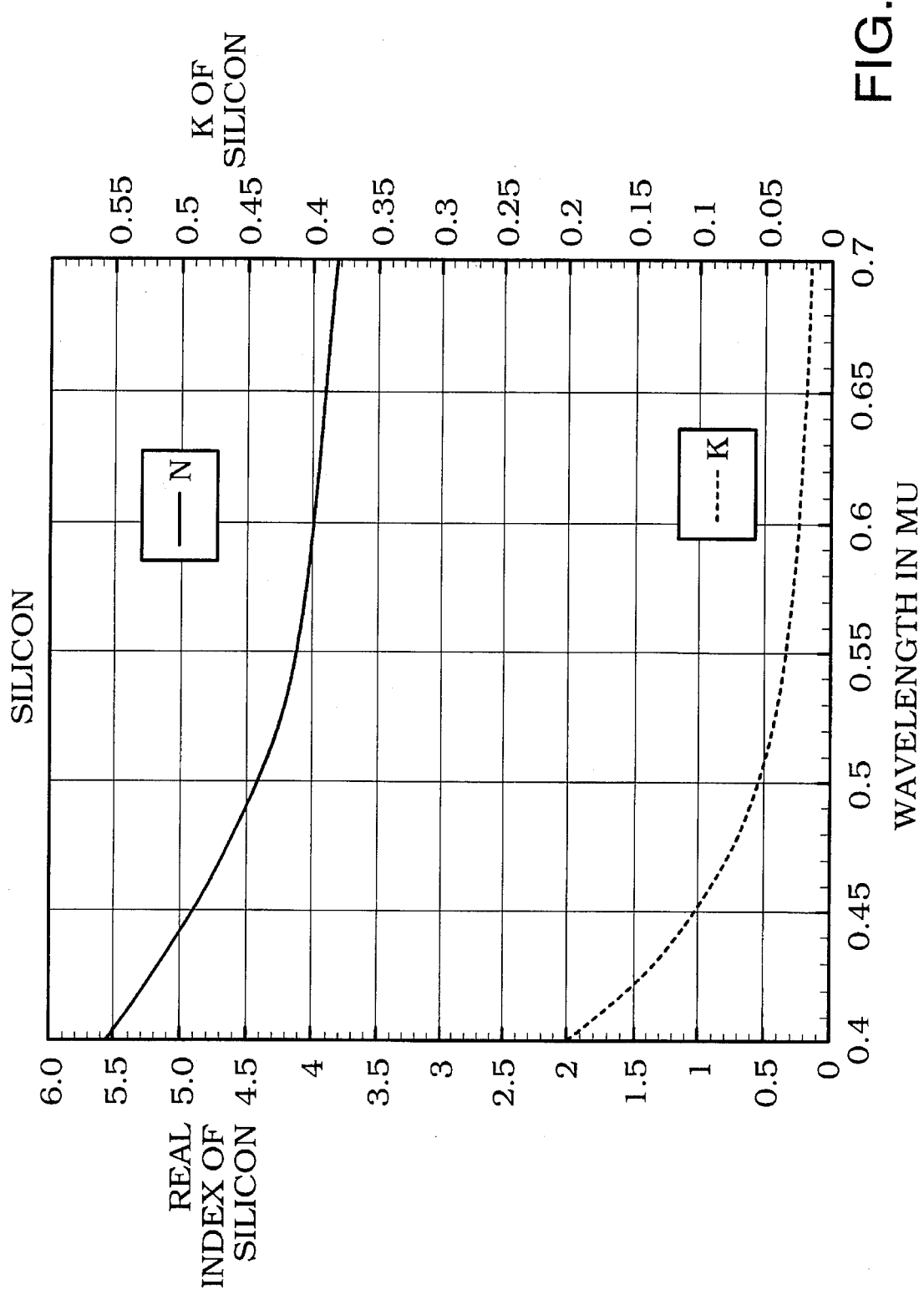

Our preferred material for use in inks and paints is silicon, whose refractive index components appear in FIG. 10. Doping silicon with impurities drawn from columns III and/or V of the periodic table results in an increase both of conductivity and absorption.

Figure 11:
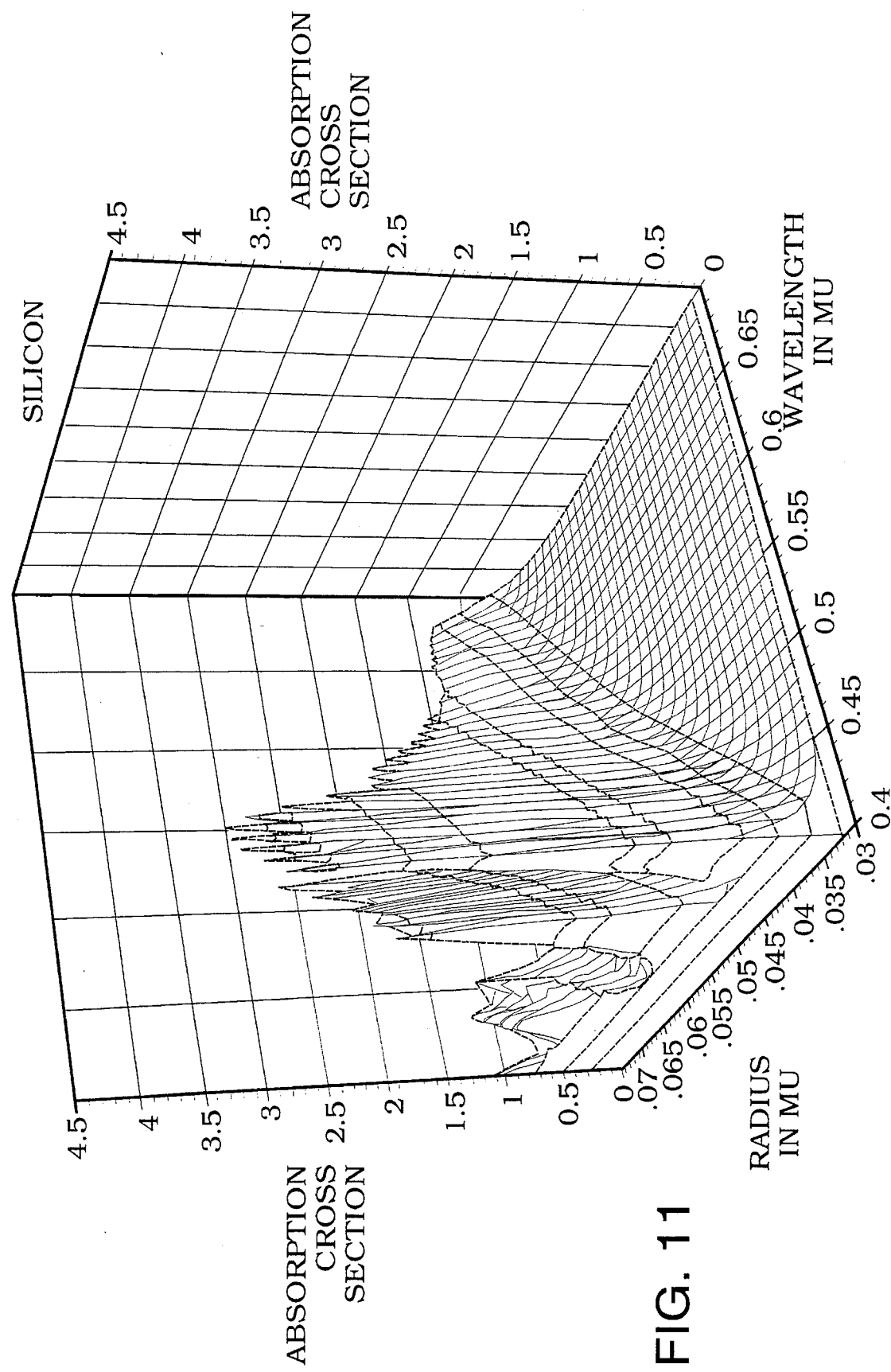

FIG. 11, which shows the absorption cross-section for undoped silicon as a function of wavelength and particle radius, reveals that particles with radii of approximately 0.04 μm exhibit a first, strong resonance in the blue spectral region between 0.4 μm and 0.5 μm. Increased particle size results in a shift of the resonance peak toward longer wavelengths. Accordingly, it is possible to "tune" the peak absorption wavelength by choosing an appropriately sized particle.

Particles having radii greater than about 0.055 μm exhibit a second, weaker resonance, also in the visible spectrum. For optimal performance as a color pigment, two absorption regions can also be employed, although the results may be less than optimal. To compensate for the unwanted second peak, one chooses materials whose intrinsic absorptions in this spectral region are either small enough to reduce the overall absorption to negligible levels notwithstanding the resonance effect, or high enough to spoil that effect entirely. The intrinsic absorption level can be increased, for example, through doping. Alloying of two resonance absorbers frequently produces performance results that vary smoothly between the behavior of the pure materials; this is true, for example, of germanium and silicon.

Figure 12:
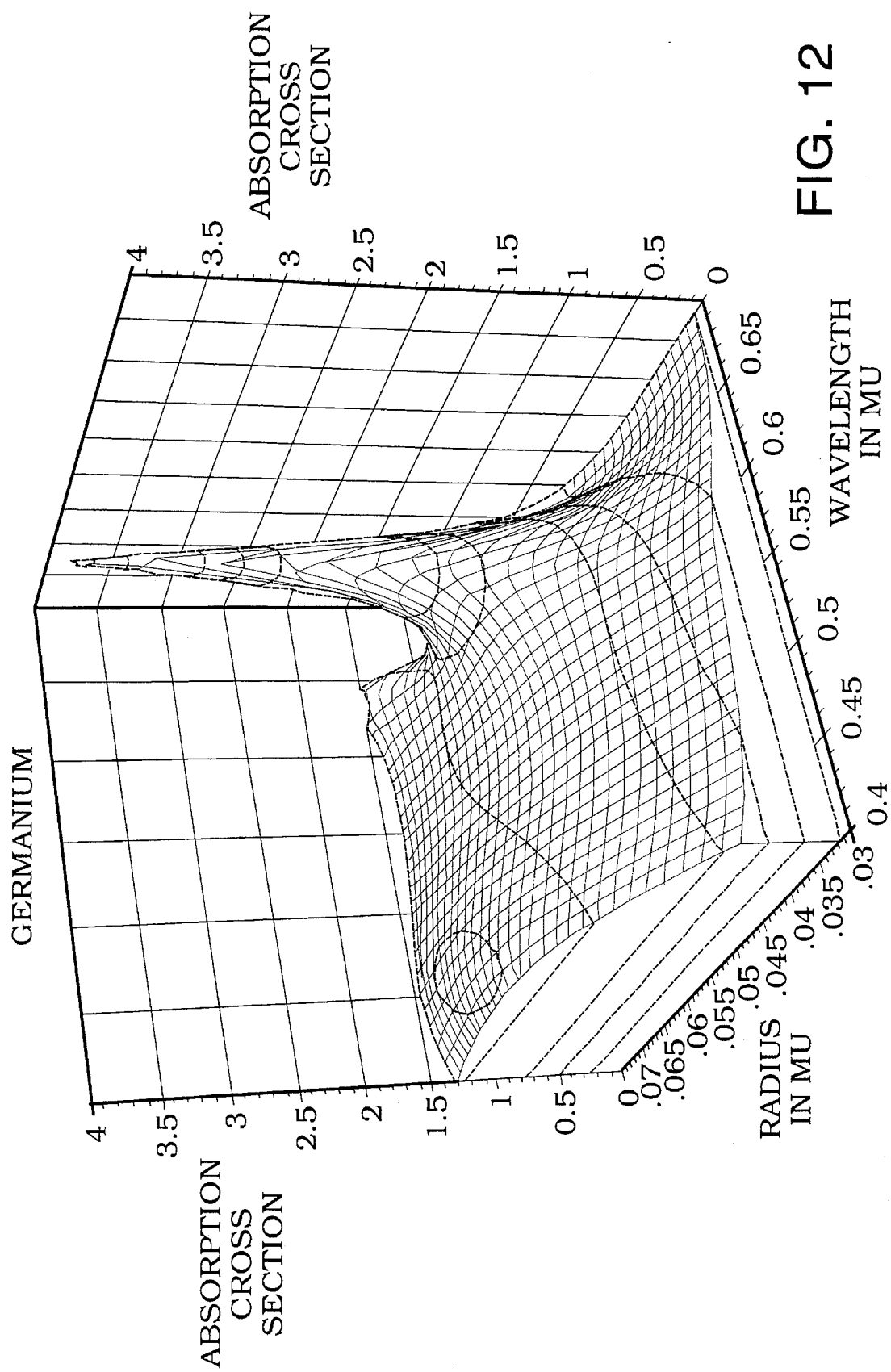
Figure 15:
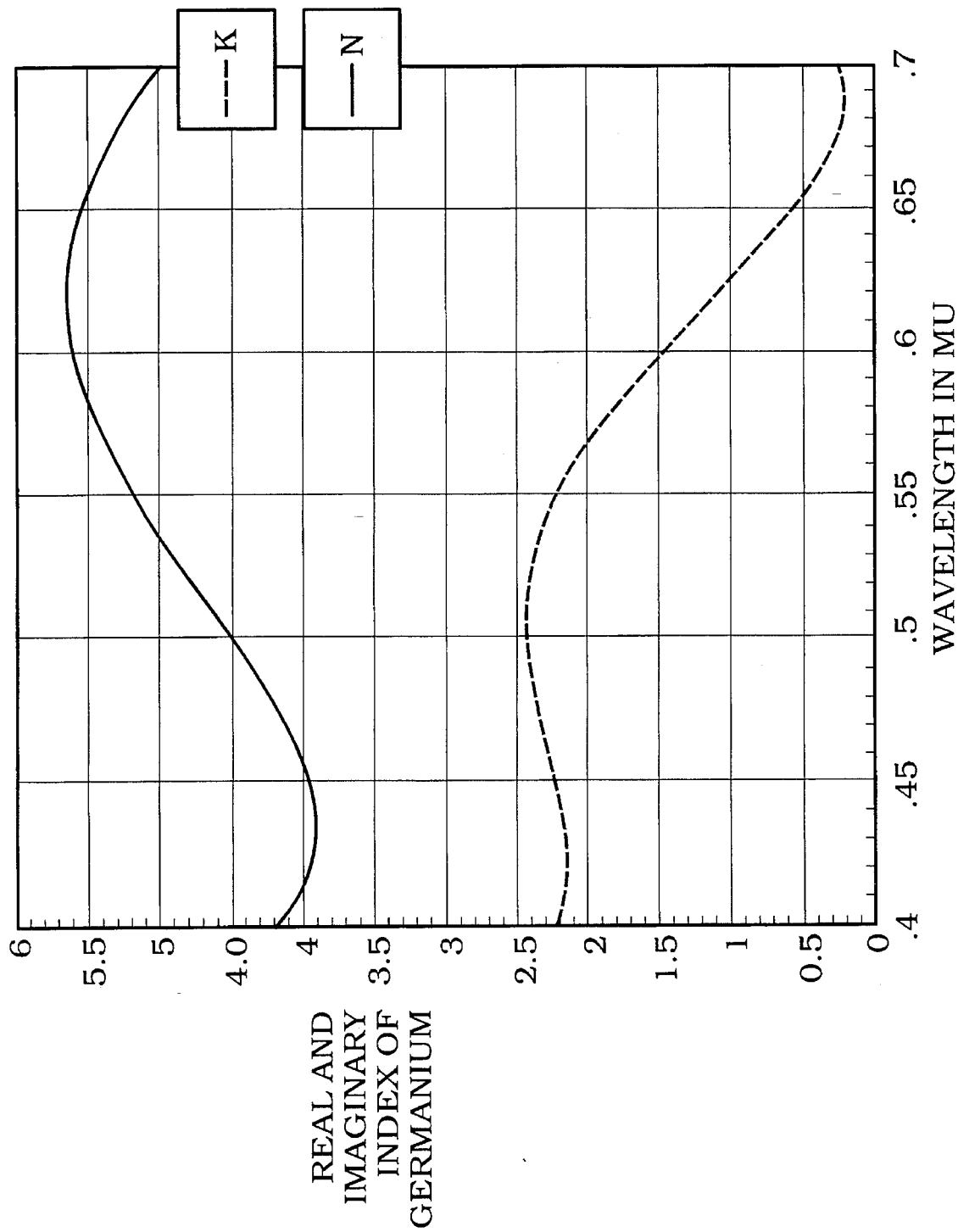
Figure 16:
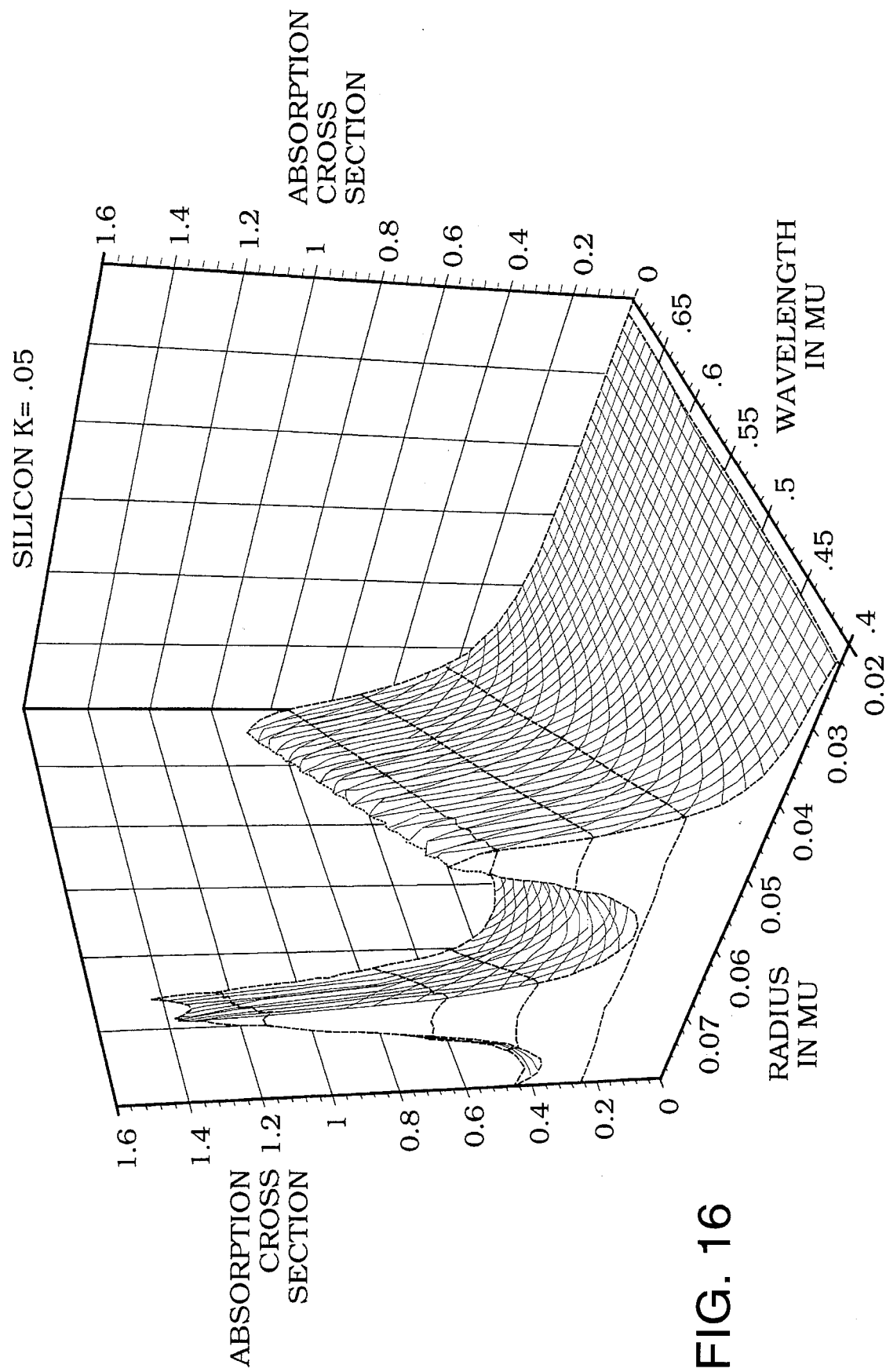
Figure 17:
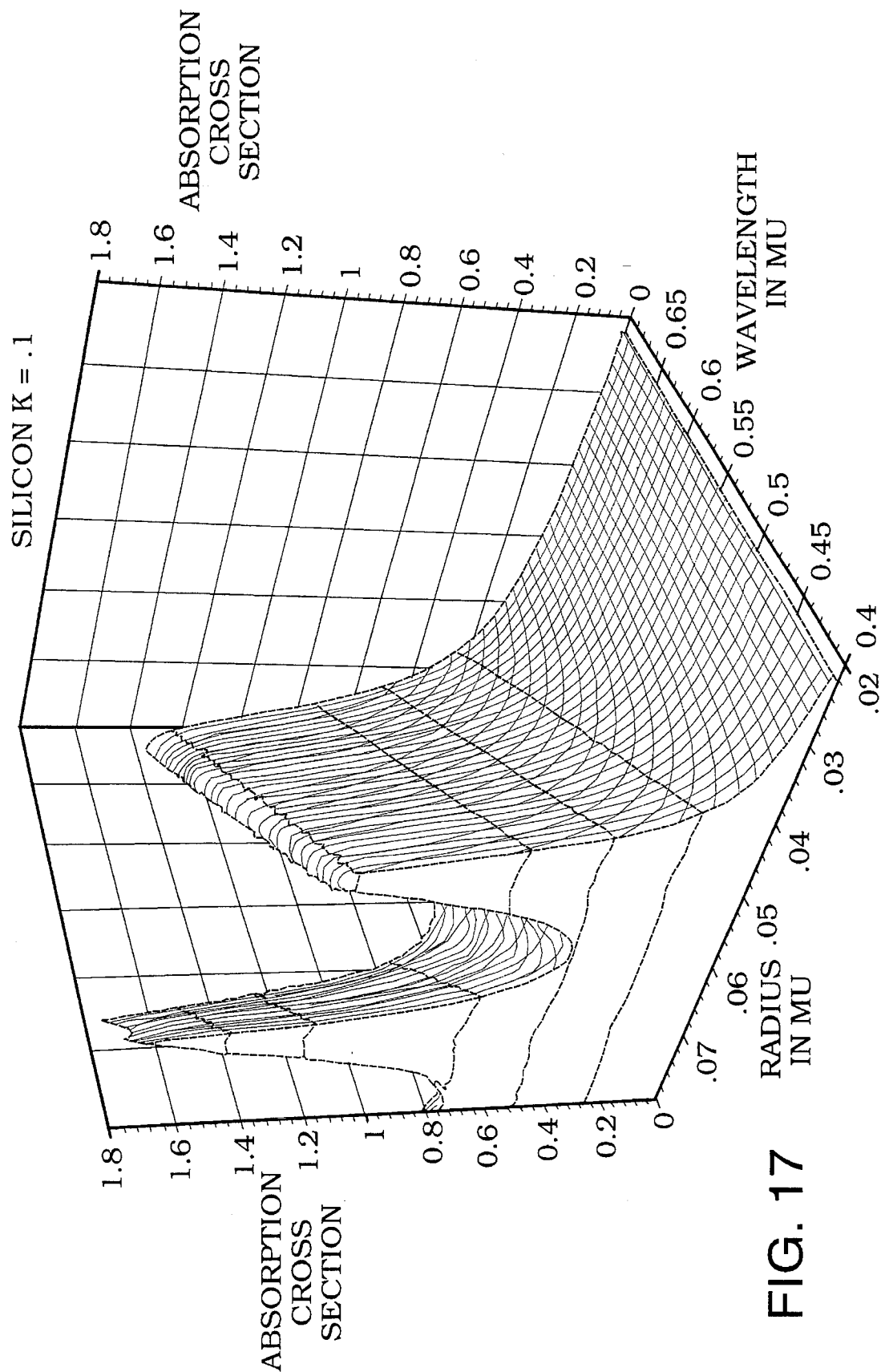
Figure 18:
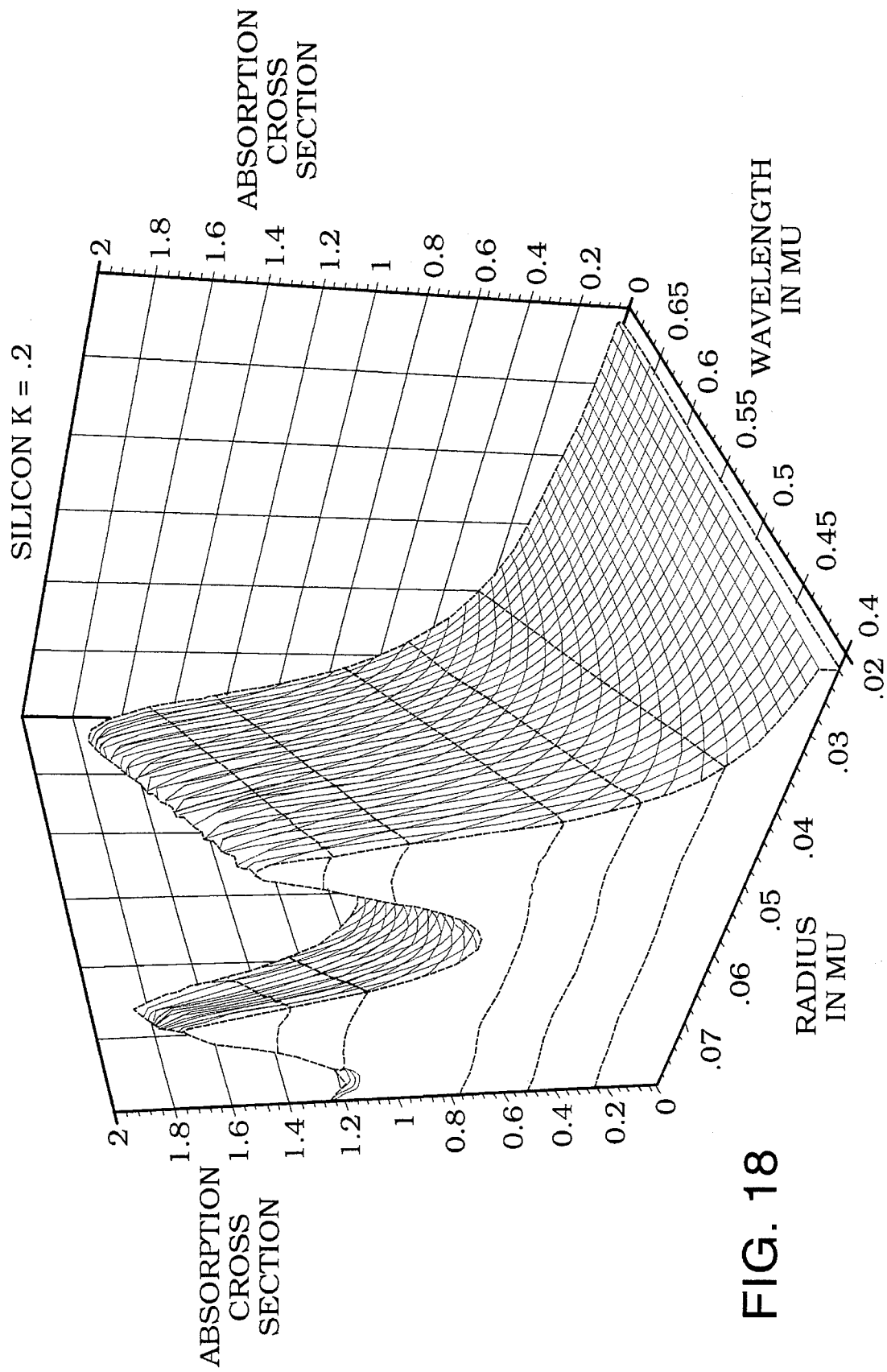
Figure 19:
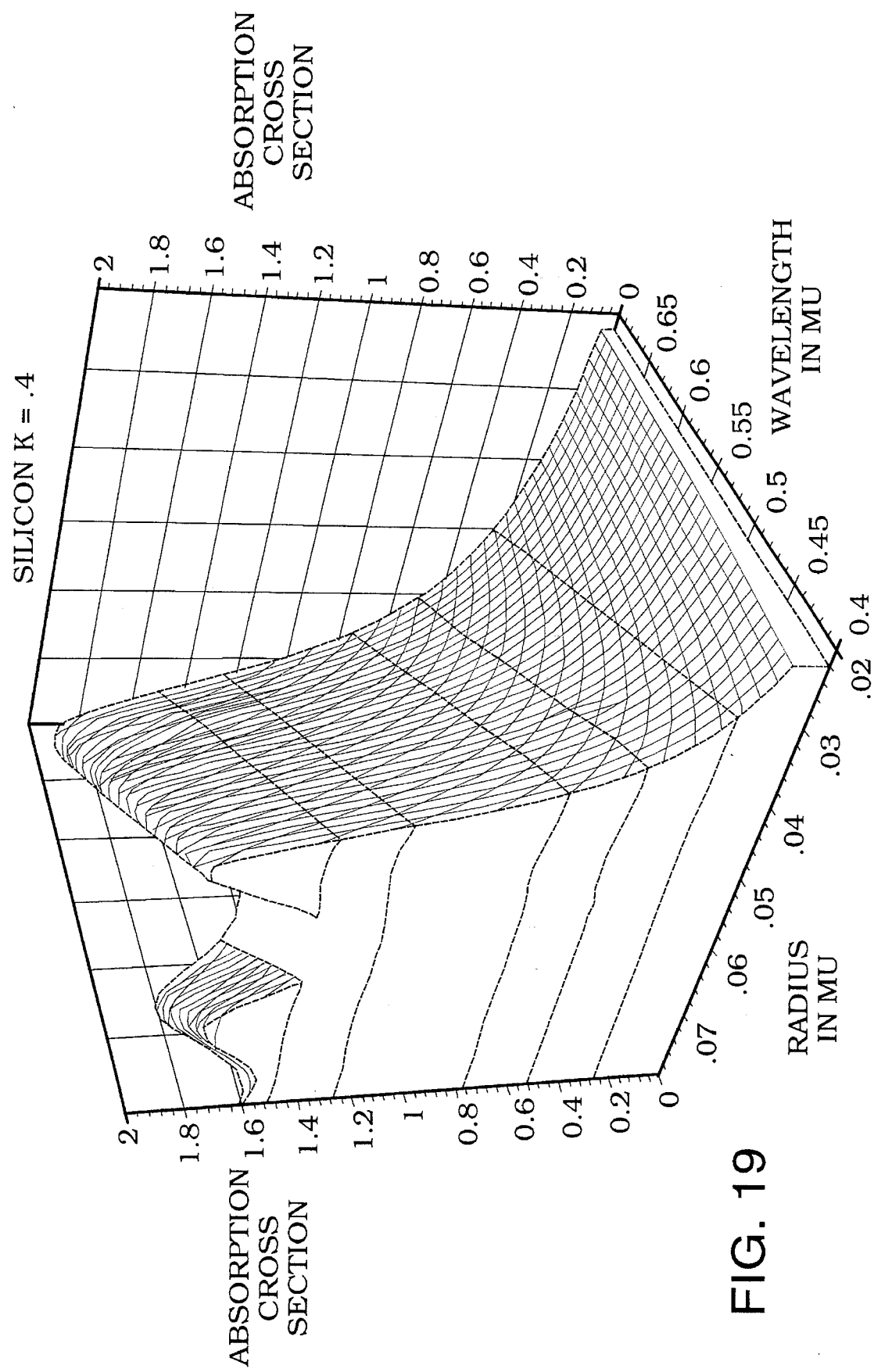
Figure 20:
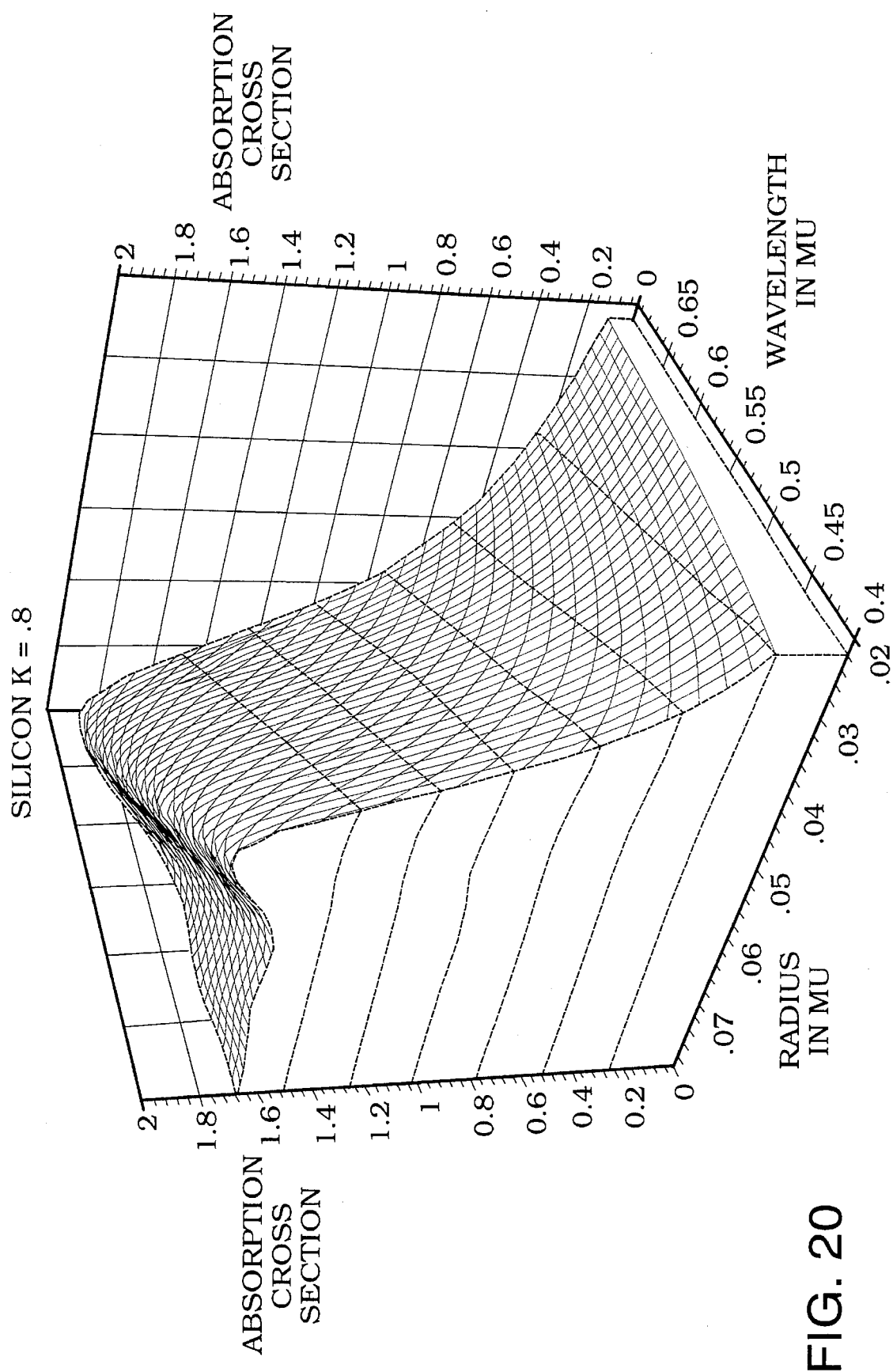

As illustrated in FIG. 12, germanium particles of radius 0.07 μm exhibit a strong resonance near the red wavelength of 0.65 μm. A partial explanation of the isolated peak appears in FIG. 15, which shows that the K refractive-index component for germanium is high over much of the visible spectrum, preventing the emergence of any strong resonances. Near 0.65 μm the magnitude of K drops to 0.5, low enough for the resonance peak to occur. The effect of K on resonance is shown explicitly in the theoretical surfaces of FIGS. 16–20, which illustrate how an increase in K gradually destroys the selectivity of the absorption process (and, therefore, optical resonance) in silicon. At a level of K=0.8 the resonance effect has essentially disappeared. Small particles, even those with high K values, exhibit small scattering and absorption cross-sections.

It is also possible to coat optically resonant particles with an intrinsically absorbing shell; judicious choice of materials can substantially increase the shell's absorption through optical resonance of the particle/shell combination. Important to this choice are the refractive index of the core particle, its size, the refractive index of the surrounding material, and the thickness of the shell; preferably, the core does not absorb substantially or at all in the wavelength regions absorbed by the shell. One chooses a core particle with a sufficiently high refractive index to guarantee substantial trapping of incident light within the core particle, and which deviates substantially (i.e., by at least 2) from the refractive index of the surrounding medium. Above a characteristic threshold refractive index difference, variation of the core index results in generation of resonance peaks for the particle/shell combination at different wavelengths. The resonance wavelength shifts proportionally to larger values as the radius of the core particles or their refractive index is increased.

Figure 21:
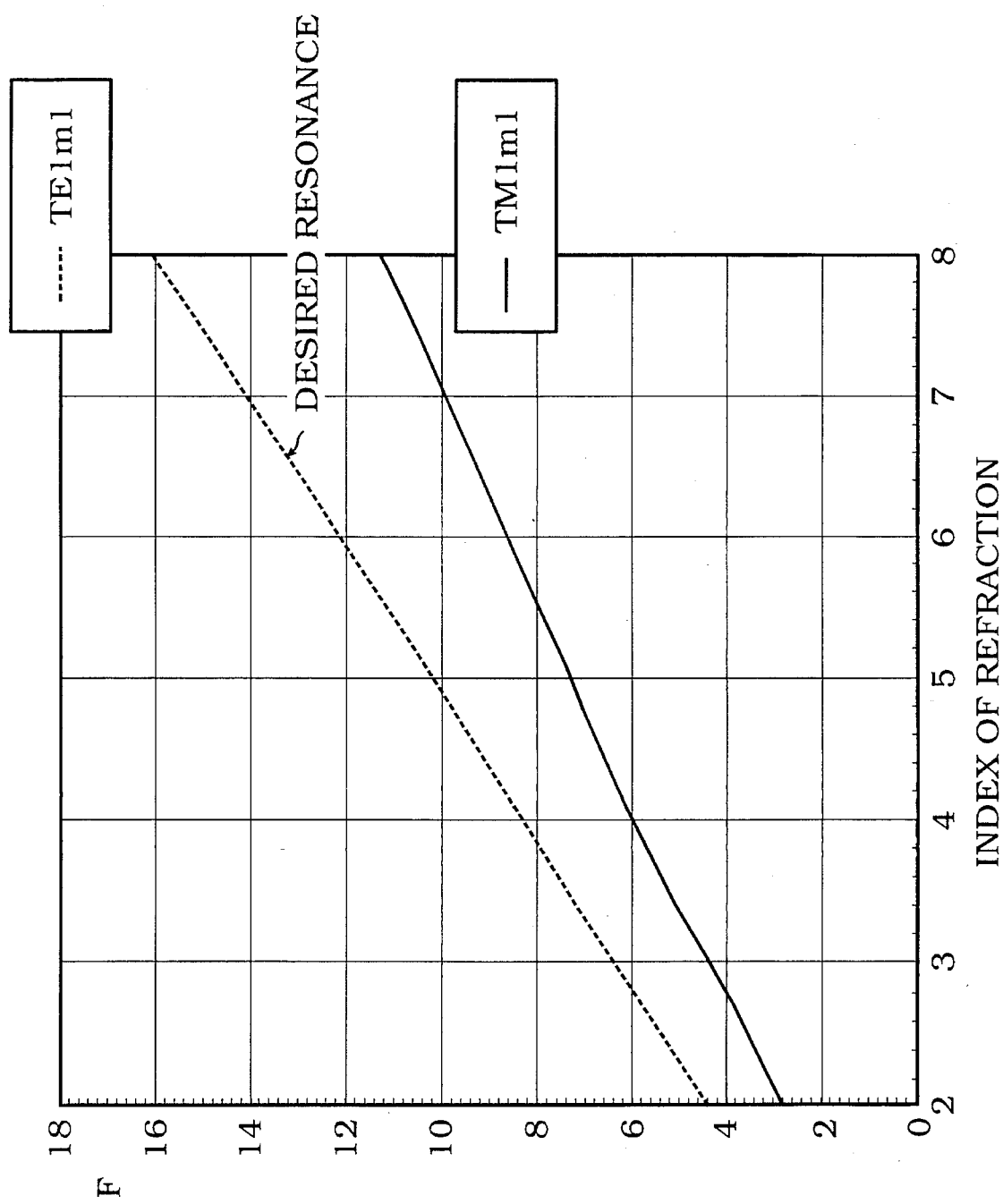

An illustrative embodiment utilizes a spherical particle of radius 0.1 μm coated with a dye shell of thickness 40 Å which, for simplicity, is assumed to have a constant (i.e., wavelength-independent) value for the imaginary refractive-index component K=0.25. As shown in FIG. 21, varying the real part of the particle's index of refraction shifts the wavelength of peak absorption cross-section, with maximum levels as high as 10. For small values of N (i.e., below 1.75) no resonance is observed; under such conditions absorption is indistinguishable from that of the free dye in solution.

It is believed that the enhancement of dye properties occurs, despite trapping of radiation within the high-index core, as a result of penetration of the evanescent wave beyond the surface of the core and into the dye layer, which absorbs energy therefrom. In other words, the core, which does not absorb in the dye's absorption spectrum, nevertheless enhances the dye's characteristic absorption by energy imparted via the evanescent wave, the magnitude of which depends on the degree of resonance.

Because the evanescent wave decays exponentially with distance from the core surface, it is useful to keep the dye layer relatively thin, preferably from 20 Å to 100 Å; while thicker layers can be used, they are largely superfluous, since only the inner portion of a thick shell absorbs most of the radiation. A thicker shell preferably exhibits a low refractive index relative to that of the core so as to avoid interfering with the core's resonance.

To construct a dye-shell pigment particle exhibiting a resonance peak at a desired wavelength, one first identifies a candidate core material having a real refractive-index component greater than that of the surrounding medium by at least 2.5 to 3. Using the Mie calculations described above, suitably modified to include a shell, one next calculates the particle size necessary to maximize $C_{abs}$ of the particle/shell combination at the dye's peak absorption wavelength.

This approach is illustrated in FIG. 21, which shows the relationship between any spherical particle's refractive index and a quantity F, which represents the ratio of the resonance wavelength to the particle radius. The transverse electrical mode $TE_{1m1}$, represents the lowest-order mode; it has an electric vector (but not a magnetic vector) which is perpendicular to the direction of wave propagation, and corresponds to the particle's first resonance and is the quantity of greater interest for our purposes; the transverse magnetic mode $TM_{1m1}$ corresponds to the next resonance, which occurs at larger particle sizes.

Using a characteristic curve such as that shown in FIG. 21 for a given core material, one can obtain, for a desired resonance wavelength, a range of particle size and refractive indices; the choice of an optimal combination of these variables is determined by the refractive index of the surrounding medium (bearing in mind the desirability of having the particle's real refractive-index component exceed that of the surrounding medium by at least 2.5 to 3) and size-dependent scattering effects. If the shell is thin and/or exhibits a low refractive index relative to that of the core, it will not materially affect the core's resonance properties as calculated using the Mie formulas.

Suitable carriers for the colored particles of the present invention include polyethylene (PE), polypropylene (PP), polymethylmethacrylate (PMMA) and copolymers such as PMMA/PBMA (polybutylmethacrylate), PMMA/PS (polystyrene), or PBMA/PS.

c. Color Filters

One can combine the absorption-edge cutoff phenomenon with optical resonance to obtain highly effective color filters. Traditional filters, such as those used in photographic applications, utilize ordinary dyes dispersed in gelatin matrices. However, the "soft shoulder" spectral absorption patterns exhibited by ordinary dyes prevent full exclusion of unwanted wavelengths. Particles of bandgap material whose absorption edge corresponds to a desired numerical wavelength cutoff value are dispersed within a carrier material, such as a thin sheet of transparent plastic or glass, at a sufficient volumetric density to effectively cover the area of the carrier, thereby preventing transmission of wavelengths shorter than cutoff value. As in the case of containers, described above, a distribution of particle sizes can be employed, since absorption depends primarily on the nature of the bandgap material rather than its geometry or size.

Because bandgap particles of proper size (which can be determined using the Mie calculations set forth above and/or FIG. 21) will frequently exhibit optical resonance, such particles can be used not only to exclude a partial spectrum of wavelengths but also to generate a very pronounced absorption peak to create color.

Figure 22:
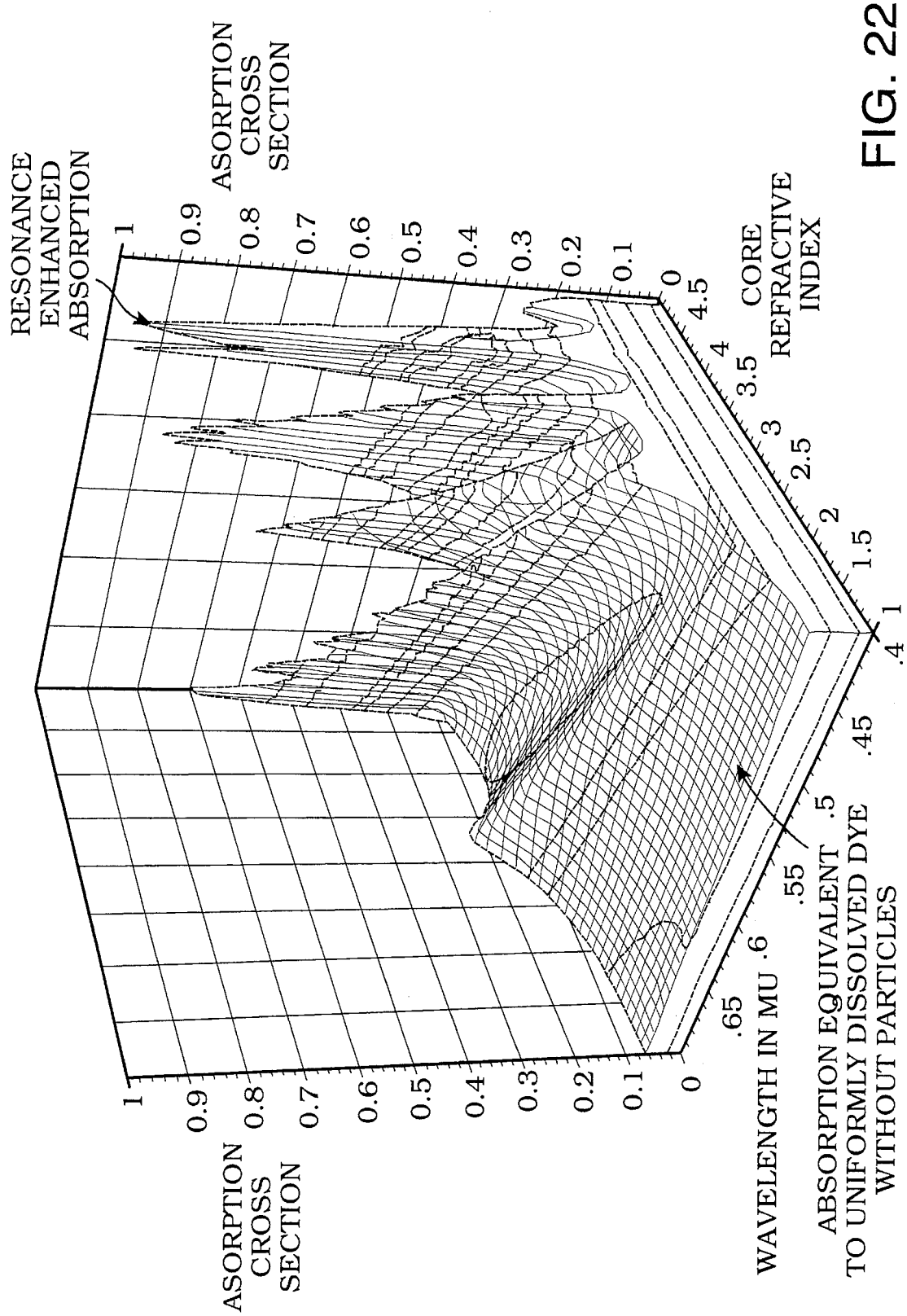

Alternatively, a dye-coated particle having deliberately mismatched refractive indices can be prepared, in the manner described above, such that an extremely strong resonance peak occurs at a specific wavelength of interest. As shown in FIG. 22, the selectivity of the resonance wavelength is highly specific and the magnitude of the absorption quite strong; absorption at the resonance wavelength will therefore eclipse all other absorption and effectively define the optical characteristics of the carrier medium (so long as the particles are present in sufficient volumetric density to effectively cover the presented area of the carrier). Dye-coated resonance particles can be used in lieu of bandgap material or in addition thereto.

The sharp absorption edge in the visible region produced by a direct semiconductor gives rise to color. An absorption edge near 0.5 μm wavelength absorbs all radiation below 0.5 μm, resulting in a yellow color. An absorption edge at 0.6 μm gives rise to a red color. The combination of resonance absorption and a bandgap absorption edge in the same particle is in general useful when the absorption edge arises from an indirect semiconductor, which exhibits a gradual absorption edge. In the absorbing region where K is less than about 0.5 (depending somewhat on the magnitude of the real component of the refractive index), a resonance can produce a much stronger absorption. This effect can be utilized to produce color. For example, silicon, which is an indirect semiconductor, can be used to produce tunable (i.e., size-dependent and selectable) colors whose intensities are particularly strong due to this enhanced absorption phenomenon.

Bandgap absorbers can be used together with resonance particles where the bandgap absorbers and the resonance particles are made of either the same or different materials. The absorption cutoff wavelength of the bandgap material is chosen to prevent passage of problematic radiation, but is less than the desired absorption peak of the dye or resonance particle. The bandgap and resonance particles are each loaded into the carrier material at sufficient volumetric density to effectively cover its presented area. This approach is also well-suited to production of inks and paints.

d. Lotions

The present invention can be utilized to produce lotions that protect human skin against harmful radiation, most importantly UV radiation. In this case particles are uniformly dispersed within a pharmacologically safe viscous carrier medium, numerous examples of which are readily available and well-known in the cosmetics and pharmaceutical arts.

For example, as noted above, titanium dioxide spheres of radius 0.075 μm satisfactorily block UV radiation in the UVA, UVB and UVC spectral regions while transmitting light of longer (and much less harmful) wavelengths; such particles also exhibit little scatter in the visible region, thereby avoiding an objectionable milky appearance. Alternatively, a bandgap material such as silicon of radius about 0.035 μm will exhibit a strong absorption peak near 0.4 μm. A distribution of particles with radii of 0.035 μm down to 0.02 μm will give rise to many overlapping absorption peaks extending from 0.4 μm to shorter wavelengths. Together these absorption peaks will effectively block virtually all UV transmission of interest over a broad wavelength band.

e. Manufacture of Particles

Figure 23:
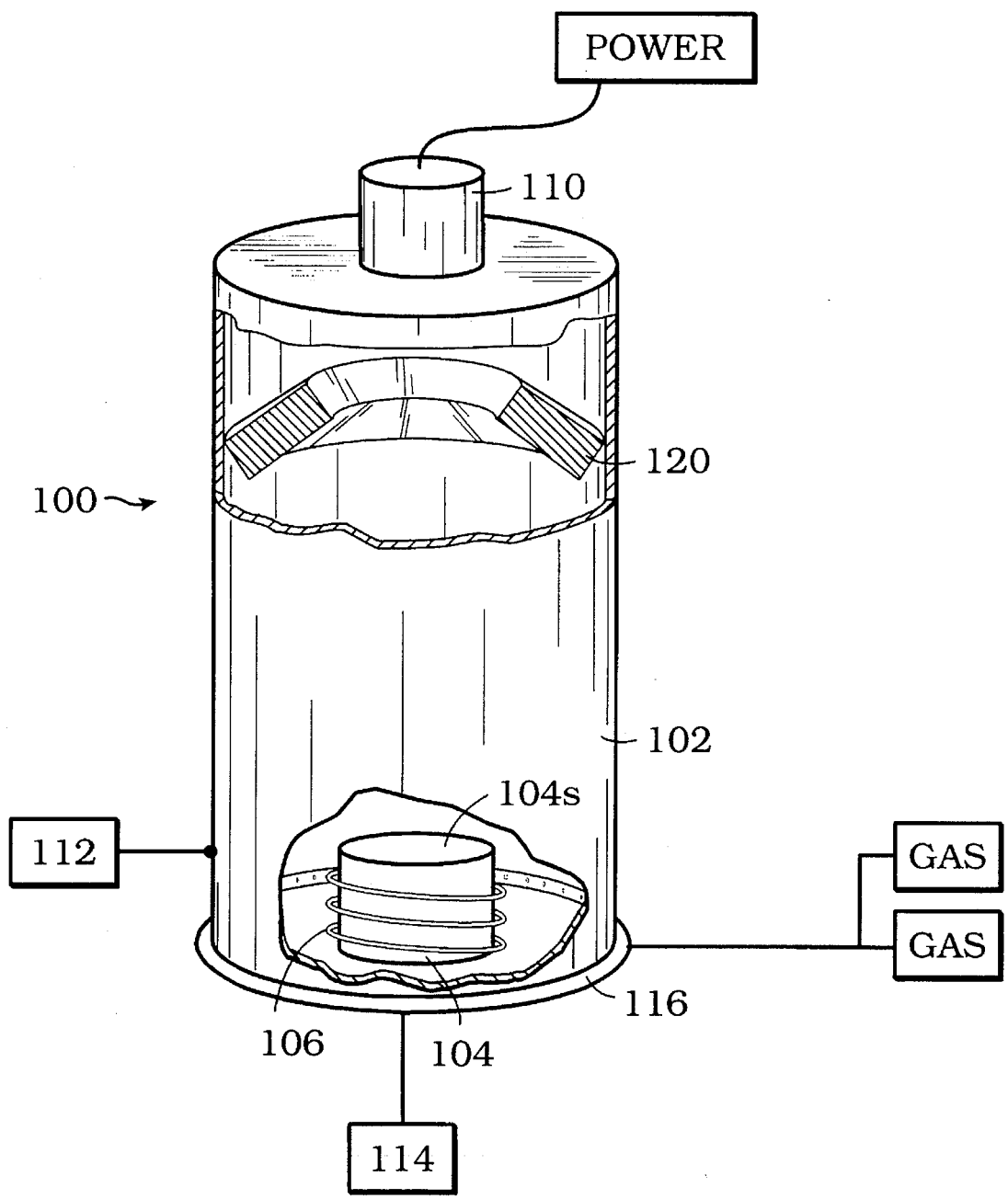

Although particles suitable for use in the application described above may be produced through any number of commercial processes, we have devised a preferred manufacturing method and apparatus for vapor-phase generation. Refer to FIG. 23, which illustrates a suitable reactor configuration indicated generally by reference numeral 100. The reactor includes a vacuum vessel 102 that contains a preheated supply rod 104, whose surface is additionally heated as described below to cause the formation of a vapor from which particles are derived. Supply rod 104 is maintained at a temperature close to its melting point by an inductive heating coil 106. An electron beam source 110, whose output is oriented toward the surface 104s of pool 104 and whose beam output is substantially coincident with the contour of surface 104s, evaporates the hot material into a vapor. To ensure that these having largely equal diameters, surface 104s is subjected to the vibration output of an ultrasound source 112. Source 112 produces, for example, a transverse acoustic wave across surface 104s. Alternatively, one can employ an ultrasound source 114, which generates a vertical ultrasound wave directed axially through supply rod 104. The respective intensities and frequencies of source 112 or 114 are adjusted so as to cause the separation from surface 104s of myriad vapor droplets having a predetermined specific, uniform size.

An inert gas (such as argon) is injected at low pressure (typically about 0.001 torr) into vessel 102 through a ring inlet 116. The inert gas sweeps the cloud of vapor droplets toward the entrance of a cryogenic pump whose chamber 120 receives both the inert gas and the solidified vapor droplets. The gas is released from a level at or below surface 104s to ensure entrainment of all generated vapor droplets. In transit to receptor 120 the droplets solidify, and in chamber 120 are frozen into a cryogenically cooled mixture of particles and inert gas. The particles are subsequently recovered from chamber 120 as a finely dispersed powder.

If desired, a reactant dopant gas can be introduced along with the inert gas to form electronegative species on the surface of the droplets during transit. Use of oxygen, for example, results in formation of oxides of the base material and attachment of atomic oxygen to the surface, the extent of reaction—i.e., the proportion of the droplet surface covered by oxygen and oxide derivatives—depends on the amount of oxygen gas introduced and the duration of droplet transit. In any case, all vapor droplets pass through the flood of electrons emitted by electron beam source 110, and thereby acquire an electrostatic potential that repels the particles from one another during their transit to chamber 120. This electrostatic charge is generally retained by the particles after they are collected from chamber 120. If desired, electronegative gas species other than oxygen, such as fluorine, can also be used advantageously.

The degree of charge imparted to the particles is preferably sufficient to confer a repulsive force among particles that exceeds their average thermokinetic energy, thereby creating effective resistance to collision and coalescence. As a further means of reducing reagglomeration, the internal geometry and operating parameters of vessel 102 can be maintained such that the distance the droplets travel before resolidifying remains below the mean free path. Ensuring the persistence of this condition requires a relatively large mean free path, which can be established by high-vacuum conditions, and rapid heat dissipation with distance from surface 104s.

It will therefore be seen that the foregoing represents a highly advantageous approach to the mass production of uniformly sized particles having selected optical and physical properties, and which may be employed in a variety of products that require finely selectable radiation-transmission and blocking (as well as chemical and mechanical) properties. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. An electromagnetic radiation-absorptive material for blocking passage of selected radiation within a spectral band, the material comprising:

a. a carrier material having a refractive index; and b. dispersed therein, a particulate material having substantially uniform particle size and exhibiting an absorption cross-section greater than 1 in the spectral band, the particulate material having a refractive index differing from that of the carrier and being present in sufficient volumetric density to substantially block passage of the selected radiation.

2. The material of claim 1 wherein the particulate material is spherical, and exhibits a real refractive-index component greater than 2 and an intrinsic absorption within the predetermined spectral band corresponding to an imaginary refractive-index component ranging from 0.02 to 0.5.

3. The material of claim 1 wherein the particle size is chosen to minimize scattering of visible radiation.

4. The material of claim 1 wherein the particulate material is a rutile crystal.

5. The material of claim 4 wherein the particulate material is titania.

6. The material of claim 4 wherein the particulate material consists of uniformly sized spheres having a diameter that ranges from 0.03 μm to 0.15 μm.

7. The material of claim 4 wherein the particulate material consists of spheres of diameter 0.075 μm.

8. The material of claim 4 wherein the volumetric density of the particulate material is approximately $1.5\times10^{11}$ particles/$cm^3$.

9. The material of claim 1 wherein the particulate material is silicon.

10. The material of claim 9 wherein the silicon is in the form of spheres of radius ranging from 0.02 μm to 0.035 μm.

11. The material of claim 9 wherein the silicon is doped with at least one element selected from Group III and/or Group V of the periodic table.

12. The material of claim 1 wherein the particulate material is germanium.

13. The material of claim 12 wherein the germanium is doped with at least one element selected from Group III and/or Group V of the periodic table.

14. The material of claim 1 wherein the particulate material comprises at least one indirect semiconductor.

15. The material of claim 1 wherein the particulate material is selected from the group consisting of aluminum phosphide, aluminum indium phosphide, aluminum arsenide, aluminum antimonide, gallium arsenide phosphide, gallium antimonide, cadmium selenide, cadmium telluride, zinc telluride, silicon, germanium, and alloys of silicon and germanium.

16. The material of claim 1 wherein the particulate material is selected from the group consisting of gallium phosphide; gallium arsenide; alloys of gallium, aluminum and arsenic; alloys of gallium, indium and nitrogen; and alloys of aluminum and antimony.

17. The material of claim 1 further comprising a second particulate material that exhibits a direct electronic bandgap whose energy corresponds to a wavelength threshold and which absorbs radiation of wavelength below the threshold, said second material being present in sufficient volumetric density to substantially block passage of the radiation of wavelength less than the threshold.

18. The material of claim 1 further comprising a second particulate material that exhibits an indirect electronic bandgap that overlaps the spectral band.

19. The material of claim 1 wherein the carrier is selected from the group consisting of polyethylene, polypropylene, polymethylmethacrylate, polystyrene, and copolymers thereof.

20. The material of claim 1 wherein the carrier and particulate materials cooperatively function as a meltable color ink.

21. The material of claim 1 wherein the carrier and particulate materials cooperatively function as a paint.

22. The material of claim 1 wherein the carrier and particulate materials cooperatively function as a lotion.

23. The material of claim 1 wherein the carrier and particulate materials form a solid, which is shaped as a container.

24. The material of claim 1 wherein the carrier and particulate materials form a solid, which functions as a colored gel.

25. The material of claim 1 wherein the refractive index of the particle exceeds that of the carrier by at least 2.5.

26. The material of claim 1 wherein the particles exhibit a mutually repulsive electrostatic charge.

27. A radiation-absorptive material for blocking passage of selected radiation having a wavelength below a threshold, the material comprising:
   a. a carrier material; and
   b. dispersed therein, a particulate material that exhibits an electronic bandgap whose energy corresponds to the wavelength threshold and which (i) absorbs radiation of wavelength below the threshold and (ii) exhibits an absorption cross-section greater than 1 in a spectral band that overlaps the wavelength threshold, the material being present in sufficient volumetric density to substantially block passage of the selected radiation.

28. The material of claim 27 wherein the particulate material comprises at least one direct semiconductor.

29. The material of claim 28 wherein the particulate material includes at least one member of the group consisting of zinc oxide, gallium nitride, gallium indium nitride, gallium arsenide, and aluminum arsenide.

30. The material of claim 27 wherein the particulate material is an alloy of two components.

31. The material of claim 27 wherein the particulate material has an average size chosen to minimize scattering of visible radiation.

32. The material of claim 27 further comprising a second particulate material having substantially uniform particle size and exhibiting an absorption cross-section greater than 1 in a spectral band that overlaps the wavelength threshold, the material being present in sufficient volumetric density to substantially block passage of radiation in the spectral band.

33. The material of claim 27 wherein the carrier and particulate materials cooperatively function as an ink.

34. The material of claim 27 wherein the carrier and particulate materials cooperatively function as a paint.

35. The material of claim 27 wherein the carrier and particulate materials cooperatively function as a lotion.

36. The material of claim 27 wherein the carrier and particulate materials form a solid, which is shaped as a container.

37. The material of claim 27 wherein the carrier and particulate materials form a solid, which functions as a colored gel.

38. The material of claim 27 wherein the particles exhibit a mutually repulsive electrostatic charge.

39. A thin polymeric or glass film containing the material of claim 1 laminated to a transparent substrate.

40. The film of claim 39 further containing the material of claim 27.

41. A thin polymeric or glass film containing the material of claim 27 laminated to a transparent substrate.

* * * * *